United States Patent [19]
Towle et al.

[11] Patent Number: 6,107,089
[45] Date of Patent: Aug. 22, 2000

[54] NUCLEIC ACIDS ENCODING ANNEXIN XI

[75] Inventors: Christine A. Towle, Wakefield; Benjamin V. Treadwell, Boston, both of Mass.

[73] Assignee: The General Hospital Corporation, Boston, Mass.

[21] Appl. No.: 08/526,136

[22] Filed: Sep. 5, 1995

Related U.S. Application Data

[63] Continuation of application No. 08/214,036, Mar. 16, 1994, abandoned, which is a continuation of application No. 07/837,775, Feb. 13, 1992, abandoned, which is a continuation-in-part of application No. 07/764,465, Sep. 23, 1991, abandoned.

[51] Int. Cl.[7] .......................... C07K 14/435; C12N 5/10; C12N 15/12; C12N 15/63
[52] U.S. Cl. .................... 435/326; 435/320.1; 536/23.5; 536/231
[58] Field of Search ................................. 536/23.5, 23.1; 435/320.1, 240.2, 326

[56] References Cited

U.S. PATENT DOCUMENTS

| | | | |
|---|---|---|---|
| 4,874,743 | 10/1989 | Wallner et al. | 514/12 |
| 4,879,224 | 11/1989 | Wallner et al. | 435/68 |
| 4,950,646 | 8/1990 | Wallner et al. | 530/350 |
| 5,258,497 | 11/1993 | Reutelingsperger et al. | 530/359 |
| 5,296,467 | 3/1994 | Reutelingsperger | 514/2 |

FOREIGN PATENT DOCUMENTS 0 330 396 A2   8/1989   European Pat. Off. .

OTHER PUBLICATIONS

Odenwald et al., Biochem. and Biophys. Res. Comm. 112:147–154, 1983.
Parente et al., Eur. J. Pharmacol. 99:233, 1984.
Maurer–Fogy et al., Eur. J. Biochem. 174:585, 1988.
Reutelingsperger et al., Eur. J. Biochem. 173:171–172, 1988.
Goulding et al., Annals Reumatic Diseases 48:843, 1989.
Huang et al., J. Biol. Chem. 262:7639, 1989.
Vostal et al., Biochem. Biophys. Res. Comm. 165:27, 1989.
Camussi et al., J. Exp. Med. 171:913, 1990.
Marki et al., FEBS Letters 264:171, 1990.
Peers et al. Am. rev. Respir. Dis. 141:s18, 1990.
Towle et al., Orthopaedic Trans. 14:343, 1990.
Towle et al., Transactions of the 36th Annual Meeting of the Orthopaedic Research Society, Feb. 1990, p. 112.
Burns et al., PNAS 86:3798–3802, May, 1989.
Scott et al., Analyt. Biochem. 149:163–165, 1985.
Pepinsky et al., J. Biol. Chem. 263:10799–10811, Aug. 5, 1988.
Hauptmann et al., Eur. J. Biochem. 185:63–71, 1989.
Venrooij, W.J., et al., Clinical and Experimental Rheumatology, vol. 7, No. 3, 1989, pp. 277–282.
Misaki, Y., et al., Journal of Biological Chemistry, vol. 269, No. 6, Feb. 1994, pp. 4240–4246.
Towle et al., Journal of Biological Chemistry, vol. 267, No. 8, Issued Mar. 15, 1992, pp. 5416–5423.
Towle et al., Biochimica et Biophysica Acta, vol. 1131, Issued Jun. 1992, pp. 223–226.
Ngo et al. 1994. The Protein Folding Problem & Teritary Structure Prediction, Merz et al., eds., Birkhauser, Boston pp. 491–495.
Bowie et al. 1990. Science 247:1306–1310.
Tokumitsu et al, "Molecular Cloning of Rabbit CAP–50 . . . ", *Biochem. Biophys. Res. Comm. 186(3)*: 1227–1235 (Aug. 1992).

*Primary Examiner*—Stephen Walsh
*Assistant Examiner*—Elizabeth C. Kemmerer
*Attorney, Agent, or Firm*—Fish & Richardson,

[57] ABSTRACT

Provided are DNA sequences, recombinant DNA molecules and hosts transformed with them which produce annexin XI polypeptides and methods of making and using these products. Also provided are antibodies generated against all or an immunogenic portion of annexin XI and methods for using these antibodies.

9 Claims, 7 Drawing Sheets

```
     TCGGAGGTGCTGCGCCTGGGACGCCCGGAGAGAGAGCTGCTTCTGCCCGCGTCCCACGTC
     TCCCCTCGCGACTCCCCACTGCCCCGTGGCCAGATCTAGCATGAGCTACCCAGGCTACCC    20
                                              M  S  Y  P  G  Y  P     7
     CCCGCCCGCAGGTGGCTACCCACCAGGTGCACCAGGTGGCGGTGCCTGGGGAGGTGCTGG    80
      P  P  A  G  G  Y  P  P  G  A  P  G  G  A  W  G  G  A  G        27
     CTACCCGCCACCCACCATGCCTCCCATTGGGCTGGATAATGTGGCCAACTATGCAGGGCA   140
      Y  P  P  P  T  M  P  P  I  G  L  D  N  V  A  N  Y  A  G  Q     47
     GTTCAACCAGGACTACCTCTCAGGAGTGGCGGCCAACATGTCCGGGACGTTTGGAGGAGC   200
      F  N  Q  D  Y  L  S  G  V  A  A  N  M  S  G  T  F  G  G  A     67
     CAACGTGCCAAACCTGTACCCGGGGGCCCCTGGGGGTGGTTACCCCCCAGTTCCCCCGGG   260
      N  V  P  N  L  Y  P  G  A  P  G  G  Y  P  P  V  P  P  G        87
     GGGGTTCGGGCAGCCCCCTCCCGCCCAGCAGCCTGTTCCTTCGTATGGAATGTACCCGCC   320
      G  F  G  Q  P  P  P  A  Q  Q  P  V  P  S  Y  G  M  Y  P  P    107
     CCCTGGAGGAAACCCCACCTCCGGGATGCCTTCATATCCGCCATACCCAGGGGCCCCTGT   380
      P  G  G  N  P  T  S  G  M  P  S  Y  P  P  Y  P  G  A  P  V    127
     GCCAGGCCAGCCCATGTTGCCCCCTGGACAGCAGCCCCCAGGGGTCTACCCTGGACAGCC   440
      P  G  Q  P  M  L  P  P  G  Q  Q  P  P  G  V  Y  P  G  Q  P    147
     GCCCATGACCTACCCTGGACAGTCACCAGTGCCACCTCCTGGGCAGCAGCCAGTGCCAAG   500
      P  M  T  Y  P  G  Q  S  P  V  P  P  P  G  Q  Q  P  V  P  S    167
     CTATCCAGGGTACTCAGGTTCTGGGACTGTCACCCCTGCCGTGTCCCCCGCTCAGTTTGG   560
      Y  P  G  Y  S  G  S  G  T  V  T  P  A  V  S  P  A  Q  F  G    187
     AAACCGAGGCACCATCACAGATGCATCTGGCTTTGACCCCCTGCGAGATGCTGAAGTCCT   620
      N  R  G  T  I  T  D  A  S  G  F  D  P  L  R  D  A  E  V  L    207
     GCGGAAGGCCATGAAGGGCTTTGGGACTGACGAGCAGGCCATCATTGACTGCCTGGGTAG   680
      R  K  A  M  K  G  F  G  T  D  E  Q  A  I  I  D  C  L  G  S    227
     TCGCTCCAACAAGCAACGACAGCAGATCCTCCTGTCGTTCAAGACAGCATATGGGAAGGA   740
      R  S  N  K  Q  R  Q  Q  I  L  L  S  F  K  T  A  Y  G  K  D    247
     TTTGATCAAAGATCTGAAATCTGAACTGTCAGGAAACTTTGAGAAGACAATCTTGGCCCT   800
      L  I  K  D  L  K  S  E  L  S  G  N  F  E  K  T  I  L  A  L    267
     GATGAAGACCCCTGTCCTCTTTGACGCTTATGAGATAAAGGAAGCTATCAAGGGGGCGGG   860
      M  K  T  P  V  L  F  D  A  Y  E  I  K  E  A  I  K  G  A  G    287
     CACTGATGAAGCCTGCCTGATCGAGATCCTGGCCTCCCGCAGCAACGAGCACATCCGGGA   920
      T  D  E  A  C  L  I  E  I  L  A  S  R  S  N  E  H  I  R  E    307
     GCTGAACAGAGTCTACAAGACAGAATTCAAAAAGACCCTGGAGGAGGCCATTCGGAGCGA   980
      L  N  R  V  Y  K  T  E  F  K  K  T  L  E  E  A  I  R  S  D    327
```

FIG. 1A

```
CACTTCAGGGCACTTCCAGCGGCTCCTCATCTCTCTCTCAGGGAAACCGGGATGAAAG   1040
 T  S  G  H  F  Q  R  L  L  I  S  L  S  Q  G  N  R  D  E  S    347

CACAAACGTGGACATGACCCTTGTCCAGAGAGATGTGCAGGAGCTCTATGCAGCTGGGGA  1100
 T  N  V  D  M  T  L  V  Q  R  D  V  Q  E  L  Y  A  A  G  E    367

GAACCGCCTGGGAACAGATGAGTCCAAGTTCAATGCGATTCTGTGCTCCCGGAGCCGGGC  1160
 N  R  L  G  T  D  E  S  K  F  N  A  I  L  C  S  R  S  R  A    397

CCACCTGGTGGCAGTTTTTAACGAGTATCAGAGGATGACAGGACGTGACATTGAGAAGAG  1220
 H  L  V  A  V  F  N  E  Y  Q  R  M  T  G  R  D  I  E  K  S    407

CATCTGCCGGGAGATGTCCGGGGACCTGGAGCAGGGCATGCTGGCTGTGGTGAAATGTCT  1280
 I  C  R  E  M  S  G  D  L  E  Q  G  M  L  A  V  V  K  C  L    427

TAAGAATACCCCAGCCTTCTTTGCTGAAAGGCTCAACAAGGCCATGAGGGGAGCCGGAAC  1340
 K  N  T  P  A  F  F  A  E  R  L  N  K  A  M  R  G  A  G  T    447

CAAAGACCGGACCCTGATCCGCATCATGGTGTCTCGCAGCGAGATCGACCTCCTGGACAT  1400
 K  D  R  T  L  I  R  I  M  V  S  R  S  E  I  D  L  L  D  I    467

CAGAGCAGAGTATAAGCGGCTGTATGGCAAGTCGCTGTACCACGACATCACGGGAGACAC  1460
 R  A  E  Y  K  R  L  Y  G  K  S  L  Y  H  D  I  T  G  D  T    487

TTCAGGGGATTACCGGAAGATTCTGCTGAAGATCTGTGGTGGCAATGACTGAGCAGTGGC  1520
 S  G  D  Y  R  K  I  L  L  K  I  C  G  G  N  D  *              507

TGGTGGGTCACTTCTGTCCACCTGCTGGCAACAGCAATGCCAGGAAAAGGCCAAAAGAAC  1580

GTTTGTCTGTTTCTAACAAATCTACAAAGTAGCCCCCAGGTGTCACAGTTCAGACCAACT  1640

GTAGAGCCTTGGCCCCATCTCCTCCCCCGCCCTCGATCCGTGCATTGTGCTTGTGCCCGA  1700

GAACCTAGTCAGTCTCGAACTCTCTCAGGACGCCTCCTCCCCATCCCGACCCCTCACAGC  1760

CTCTTGCAGCTTAAAGTAGATGTTTTGTTCCTGAAAAATAAACTCTGGCTTCCTCTAGTC  1820

ATGTAGTTTTGTATGTTTAGAGGTTTTTTTTTTTTTTAATAATTAGTTGCAGACAGTT    1880

GCATACACATCTTTGCTGCATACAAAGTTTGGATAAAAGAGGTGGGGGGTTGGAGTGCCA  1940

TGTCTTCACTGAGGAGTAAAAGGAAAACTTTCAGGATAGACTCTGCATCTGGTGAAAATG  2000

TGTCATGAGCTTTGTTGTTGCCAAACTCACTCCTTTTTAGAAAAGAAAAGGCCAGAAAGT  2060

CATCTGTTCTTTCTTCTACACAAACCACAAGAACAAAGCCAGCTCCCTGCCAGTGACAGG  2120
    105>
GCTTCTTGTAATTGAGAATGTGCCTTAACCTGAATGTTGATGGCCAAATGCTGTTTCCAA  2180
     . 101>     .
ATTAAAGTCTGCCAGCTCTGAAAA  2204
(SEQ ID NO:2)
```

K S S K G G P G S A V S P     I
H S T P P S A Y G S V K A     II
A S I W V G H R G T V R D     III
* * * M A A K G G T V K A     IV
* * M A Q V L R G T V T D     V
P A Q G A K Y R G S I H D     VIA
A V A R V E L K G T V R P     VIB
A T V T Q V T Q G T I R P     VII
K S W I E Q E G V T V K S     VIII
```

```
E S T N V _ D M Y L V Q R D

E D F G V _ N E D L A D S D   I
E D G S V I D Y E L I D Q D   II
E S L K V _ D E H L A K Q D   III
E S N Y L _ D D A L M R Q D   IV
P D A G I _ D E A Q V E Q D   V
E D D V V _ S E D L V Q Q D   VIa
L D Q A R _ E D A Q V A A E   VIb
E N Q S I _ N H Q M A Q E D   VII
D V S S F V D P A L A L Q D   VIII
```

FIG. 3

| | | | | | |
|---|---|---|---|---|---|
| TCGGAGGTGC | TGCGCCTGGG | ACGCCCGGAG | AGAGAGCTGC | TTCTGCCCGC | 50 |
| GTCCCACGTC | TCCCCTCGCG | ACTCCCCACT | GCCCCGTGGC | CAGATCTAGC | 100 |
| CATGAGCTAC | CCAGGCTACC | CCCCGCCCGC | AGGTGGCTAC | CCACCAGGTG | 150 |
| CACCAGGTGT | CCCGGAGCTG | GAAAGCCACG | CTGGAGGCCC | CCAGGGCCTT | 200 |
| TTCGCTGCCA | TGGACAGGGC | TGTTTCTGAC | GGGCCAGCCA | TGATGCTAGC | 250 |
| TGCTGTGCTA | CTTGTGAGGG | CTACGGCGGC | CAACATGTCC | GGGACGTTTG | 300 |
| GAGGAGCCAA | CGTGCCAAAC | CTGTACCCGG | GGGCCCCTGG | GGGTGGTTAC | 350 |
| CCCCCAGTTC | CCCCGGGGGG | GTTCGGGCAG | CCCCCTCCCG | CCCAGCAGCC | 400 |
| TGTTCCTTCG | TATGGAATGT | ACCCGCCCCC | TGGAGGAAAC | CCCACCTCCG | 450 |
| GGATGCCTTC | ATATCCGCCA | TACCCAGGGG | CCCCTGTGCC | AGGCCAGCCC | 500 |
| ATGTTGCCCC | CTGGACAGCA | GCCCCAGGG | GTCTACCCTG | ACAGCCGCC | 550 |
| CATGACCTAC | CCTGGACAGT | CACCAGTGCC | ACCTCCTGGG | CAGCAGCCAG | 600 |
| TGCCAAGCTA | TCCAGGGTAC | TCAGGTTCTG | GGACTGTCAC | CCCTGCCGTG | 650 |
| TCCCCCGCTC | AGTTTGGAAA | CCGAGGCACC | ATCACAGATG | CATCTGGCTT | 700 |
| TGACCCCCTG | CGAGATGCTG | AAGTCCTGCG | GAAGGCCATG | AAGGGCTTTG | 750 |
| GGACTGACGA | GCAGGCCATC | ATTGACTGCC | TGGGTAGTCG | CTCCAACAAG | 800 |
| CAACGACAGC | AGATCCTCCT | GTCGTTCAAG | ACAGCATATG | GGAAGGATTT | 850 |
| GATCAAAGAT | CTGAAATCTG | AACTGTCAGG | AAACTTTGAG | AAGACAATCT | 900 |
| TGGCCCTGAT | GAAGACCCCT | GTCCTCTTTG | ACGCTTATGA | GATAAAGGAA | 950 |
| GCTATCAAGG | GGGCGGGCAC | TGATGAAGCC | TGCCTGATCG | AGATCCTGGC | 1000 |
| CTCCCGCAGC | AACGAGCACA | TCCGGGAGCT | GAACAGAGTC | TACAAGACAG | 1050 |
| AATTCAAAAA | GACCCTGGAG | GAGGCCATTC | GGAGCGACAC | TTCAGGGCAC | 1100 |
| TTCCAGCGGC | TCCTCATCTC | TCTCTCTCAG | GGAAACCGGG | ATGAAAGCAC | 1150 |
| AAACGTGGAC | ATGACCCTTG | TCCAGAGAGA | TGTGCAGGAG | CTCTATGCAG | 1200 |
| CTGGGGAGAA | CCGCCTGGGA | ACAGATGAGT | CCAAGTTCAA | TGCGATTCTG | 1250 |
| TGCTCCCGGA | GCCGGGCCCA | CCTGGTGGCA | GTTTTTAACG | AGTATCAGAG | 1300 |
| GATGACAGGA | CGTGACATTG | AGAAGCAT | CTGCCGGGAG | ATGTCCGGGG | 1350 |
| ACCTGGAGCA | GGGCATGCTG | GCTGTGGTGA | AATGTCTTAA | GAATACCCCA | 1400 |
| GCCTTCTTTG | CTGAAAGGCT | CAACAAGGCC | ATGAGGGGAG | CCGGAACCAA | 1450 |
| AGACCGGACC | CTGATCCGCA | TCATGGTGTC | TCGCAGCGAG | ATCGACCTCC | 1500 |
| TGGACATCAG | AGCAGAGTAT | AAGCGGCTGT | ATGGCAAGTC | GCTGTACCAC | 1550 |
| GACATCACGG | GAGACACTTC | AGGGGATTAC | CGGAAGATTC | TGCTGAAGAT | 1600 |
| CTGTGGTGGC | AATGACTGAG | CAGTGGCTGG | TGGGTCACTT | CTGTCCACCT | 1650 |
| GCTGGCAACA | GCAATGCCAG | GAAAAGGCCA | AAAGAACGTT | TGTCTGTTTC | 1700 |
| TAACAAATCT | ACAAAGTAGC | CCCCAGGTGT | CACAGTTCAG | ACCAACTGTA | 1750 |
| GAGCCTTGGC | CCCATCTCCT | CCCCCGCCCT | CGATCCGTGC | ATTGTGCTTG | 1800 |
| TGCCCGAGAA | CCTAGTCAGT | CTCGAACTCT | CTCAGGACGC | CTCCTCCCCA | 1850 |
| TCCCGACCCC | TCACAGCCTC | TTGCAGCTTA | AAGTAGATGT | TTTGTTCCTG | 1900 |
| AAAAATAAAC | TCTGGCTTCC | TCTAGTCATG | TAGTTTTGTA | TGTTTAGAGG | 1950 |
| TTTTTTTTTT | TTTTTAATA | ATTAGTTGCA | GACAGTTGCA | TACACATCTT | 2000 |
| TGCTGCATAC | AAAGTTTGGA | TAAAAGAGGT | GGGGGGTTGG | AGTGCCATGT | 2050 |
| CTTCACTGAG | GAGTAAAAGG | AAAACTTTCA | GGATAGACTC | TGCATCTGGT | 2100 |
| GAAAATGTGT | CATGAGCTTT | GTTGTTGCCA | AACTCACTCC | TTTTTAGAAA | 2150 |
| AGAAAAGGCC | AGAAAGTCAT | CTGTTCTTTC | TTCTACACAA | ACCACAAGAA | 2200 |
| CAAAGCCAGC | TCCCTGCCAG | TGACAGGGCT | TCTTGTAATT | GAGAATGTGC | 2250 |
| CTTAACCTGA | ATGTTGATGG | CCAAATGCTG | TTTCCAAATT | AAAGTCTGCC | 2300 |
| AGCTCTGAAA | A | | | | 2311 |

(SEQ ID NO: 3)

FIG. 4

```
Met Ser Tyr Pro Gly Tyr Pro Pro Pro Ala Gly Gly Tyr Pro Pro Gly
            5               10                  15
Ala Pro Gly Val Pro Glu Leu Glu Ser His Ala Gly Gly Pro Gln Gly
            20              25                  30
Leu Phe Ala Ala Met Asp Arg Ala Val Ser Asp Gly Pro Ala Met Met
        35              40                  45
Leu Ala Ala Val Leu Leu Val Arg Ala Thr Ala Ala Asn Met Ser Gly
    50              55                  60
Thr Phe Gly Gly Ala Asn Val Pro Asn Leu Tyr Pro Gly Ala Pro Gly
65              70                  75                      80
Gly Gly Tyr Pro Pro Val Pro Pro Gly Gly Phe Gly Gln Pro Pro Pro
                85              90                  95
Ala Gln Gln Pro Val Pro Ser Tyr Gly Met Tyr Pro Pro Pro Gly Gly
            100             105                 110
Asn Pro Thr Ser Gly Met Pro Ser Tyr Pro Pro Tyr Pro Gly Ala Pro
        115             120                 125
Val Pro Gly Gln Pro Met Leu Pro Pro Gly Gln Gln Pro Pro Gly Val
    130             135                 140
Tyr Pro Gly Gln Pro Pro Met Thr Tyr Pro Gly Gln Ser Pro Val Pro
145             150                 155                     160
Pro Pro Gly Gln Gln Pro Val Pro Ser Tyr Pro Gly Tyr Ser Gly Ser
                165             170                 175
Gly Thr Val Thr Pro Ala Val Ser Pro Ala Gln Phe Gly Asn Arg Gly
            180             185                 190
Thr Ile Thr Asp Ala Ser Gly Phe Asp Pro Leu Arg Asp Ala Glu Val
        195             200                 205
Leu Arg Lys Ala Met Lys Gly Phe Gly Thr Asp Glu Gln Ala Ile Ile
    210             215                 220
Asp Cys Leu Gly Ser Arg Ser Asn Lys Gln Arg Gln Gln Ile Leu Leu
225             230                 235                     240
Ser Phe Lys Thr Ala Tyr Gly Lys Asp Leu Ile Lys Asp Leu Lys Ser
                245             250                 255
Glu Leu Ser Gly Asn Phe Glu Lys Thr Ile Leu Ala Leu Met Lys Thr
            260             265                 270
Pro Val Leu Phe Asp Ala Tyr Glu Ile Lys Glu Ala Ile Lys Gly Ala
        275             280                 285
Gly Thr Asp Glu Ala Cys Leu Ile Glu Ile Leu Ala Ser Arg Ser Asn
    290             295                 300
Glu His Ile Arg Glu Leu Asn Arg Val Tyr Lys Thr Glu Phe Lys Lys
305             310                 315                     320
Thr Leu Glu Glu Ala Ile Arg Ser Asp Thr Ser Gly His Phe Gln Arg
                325             330                 335
Leu Leu Ile Ser Leu Ser Gln Gly Asn Arg Asp Glu Ser Thr Asn Val
            340             345                 350
Asp Met Thr Leu Val Gln Arg Asp Val Gln Glu Leu Tyr Ala Ala Gly
        355             360                 365
Glu Asn Arg Leu Gly Thr Asp Glu Ser Lys Phe Asn Ala Ile Leu Cys
    370             375                 380
Ser Arg Ser Arg Ala His Leu Val Ala Val Phe Asn Glu Tyr Gln Arg
385             390                 395                     400
Met Thr Gly Arg Asp Ile Glu Lys Ser Ile Cys Arg Glu Met Ser Gly
                405             410                 415
Asp Leu Glu Gln Gly Met Leu Ala Val Val Lys Cys Leu Lys Asn Thr
            420             425                 430
Pro Ala Phe Phe Ala Glu Arg Leu Asn Lys Ala Met Arg Gly Ala Gly
        435             440                 445
Thr Lys Asp Arg Thr Leu Ile Arg Ile Met Val Ser Arg Ser Glu Ile
    450             455                 460
Asp Leu Leu Asp Ile Arg Ala Glu Tyr Lys Arg Leu Tyr Gly Lys Ser
465             470                 475                     480
Leu Tyr His Asp Ile Thr Gly Asp Thr Ser Gly Asp Tyr Arg Lys Ile
                485             490                 495
Leu Leu Lys Ile Cys Gly Gly Asn Asp
            500             505
```

FIG. 5 (SEQ ID NO: 4)

EXONS

ACCEPTOR  DONOR

5'-common
...CCAGGTGCAC<u>CAG</u><u>gtaagaagg</u>...
   P  G  A  P (G)

B-specific
...ctg<u>gggagctctgtcctag</u>GTGTCCCGGAG.....GTGAGGGCT<u>ACG</u><u>gtgagggct</u>...
                    V  P  E     V  R  A  T

A-specific
...gact<u>gggtgttgctttcag</u>GTGGCGGTGCC.....CTCTCAGGA<u>GT</u><u>Ggtgagtcca</u>...
                 G  G  A     L  S  G  V

3'-common
...ctgc<u>tttgtggactttcag</u>GCGGCCAACATG....
                A  A  N  M

FIG. 6

NUCLEIC ACIDS ENCODING ANNEXIN XI

This is a continuation of application Ser. No. 08/214,036 filed on Mar. 16, 1994, now abandoned which is a continuation of application Ser. No. 07/837,775, filed on Feb. 13, 1992, now abandoned, which is a continuation-in-part of application Ser. No. 07/764,465, filed on Sep. 23, 1991, now abandoned.

This invention was made with Government support under Grant AM 16265 awarded by the National Institutes of Health. The Government has certain rights in the invention.

BACKGROUND OF THE INVENTION

The invention relates to DNA sequences, recombinant DNA molecules and processes for producing annexin XI as well as methods for using annexin XI.

The annexins (or lipocortins) are a family of more than ten structurally related proteins. Annexins have been identified in a variety of eukaryotes from slime molds to mammals and higher plants, and the cDNAs encoding eight distinct mammalian annexins have been sequenced. All annexins have a conserved core domain and a highly variable amino terminal domain. The core domain consists of a 60–70 amino acid motif which is repeated four times in the smaller annexins (30–50 kD) and eight times in the larger annexins (~70 kD). The amino acid sequence of this core domain is 45 to 65% conserved between various annexins. For a given annexin the entire amino acid sequence is roughly 90% conserved between different mammalian species.

Annexins bind phospholipids and $Ca^{2+}$ and associate with membrane preparations in a $Ca^{2+}$-dependent manner. Analysis of proteolytic fragments of several annexins indicates that the phospholipid and $Ca^{2+}$ binding sites lie within the conserved core domain. Many, if not all, annexins inhibit phospholipase $A_2$ ($PLA_2$), an enzyme which releases fatty acids (e.g., arachidonic acid) esterified at the $S_N2$ position of membrane phospholipids. It is thought that annexins inhibit $PLA_2$ activity by binding to phospholipids and blocking their interaction with $PLA_2$. Arachidonic acid is a precursor in the synthesis of compounds, such as prostaglandins and leukotrienes, that are involved in inflammation. The lysophospholipids and their derivatives, such as platelet activating factor (PAF), may also promote inflammatory responses. Accordingly, it has been suggested that annexins may be useful for the treatment of inflammation. Purified annexins have been shown to have anti-inflammatory activity in vivo (Parente et al., *Eur. J. Pharmacol.* 99:233, 1984). Unlike many non-steroidal anti-inflammatory compounds, annexins have the potential to block an earlier step in the eicosanoid-generated production of inflammatory substances, via the cyclooxygenase pathway or the lipoxygenase pathway as well as via lysophospholipids and related mediators.

It has been suggested that annexins may have anti-coagulant activity. Factor $X_a$-catalyzed activation of prothrombin, an important step in coagulation, is accelerated by protein cofactor $V_a$ and negatively charged phospholipids. Thus, annexins, by virtue of their ability to bind phospholipids, might inhibit prothrombin activation. Reutelingsperger et al. (*Eur. J. Biochem.* 173:171, 1988) describe an inhibitor of blood coagulation, VAC (annexin V), isolated from the intima of bovine aorta. This protein binds phospholipids in a $Ca^{2+}$-dependent manner. In a purified coagulation system this protein inhibited activation of prothrombin by factor $X_a$.

Odenwald et al. (*Biochem. and Biophys. Res. Comm.* 112:147, 1983) disclose a 56 kD annexin-like protein (synexin II) isolated from bovine adrenal medulla and liver. Odenwald et al. report that synexin-II enhances $Ca^{2+}$-induced aggregation of chromaffin granule membranes and that this activity is protease resistant.

Towle et al. (Transactions of the 36th Annual Meeting of the Orthopaedic Research Society, February, 1990) report the use of antibodies raised against an anti-collagenase activator protein (stromelysin) to identify a clone in an interleukin-1 stimulated bovine chondrocyte cDNA expression library. Towle et al. report that partial sequence analysis of this clone predicts that it encodes a protein similar to lipocortins (annexins) I and II as well as PP4X (annexin IV). Northern analysis indicated that the steady state level of RNA capable of hybridizing to this cDNA clone increases four-fold upon exposure of chondrocytes to interleukin-1.

Towle et al. (*Orthopaedic Trans.* 14:343, 1990) describe a clone cp4x, isolated from a bovine cartilage cDNA library. A cartilage protein, immunologically cross-reactive with the fusion protein encoded by cp4x, co-purified (during initial purification steps) with other annexins. The clone encodes a protein that co-purifies with annexins and is homologous to pp4x (annexin IV). Towle et al. report that the steady state level of mRNA encoding cp4x is lower in interleukin-1 stimulated bovine chondrocytes than in non-stimulated chondrocytes.

Wallner et al. (U.S. Pat. No. 4,950,646) report the isolation of a cDNA encoding a 363 amino acid human lipocortin. *E. coli* or yeast transformed with a plasmid capable of expressing the lipocortin cDNA produce a 37 kD protein that is not produced in untransformed cells. Wallner et al. also report the isolation of a partial cDNA clone of a second lipocortin, N-lipocortin, which is homologous to their originally isolated lipocortin.

Wallner et al. (European Patent Application 0 330 396) report the isolation of cDNAs encoding human lipocortins III and V and the purification of bovine lipocortins IV and VI.

Huang et al. (*J. Biol. Chem.* 262:7639, 1989) report the identification of several proteolytic fragments of human lipocortin (annexin) I that are capable of inhibiting phospholipase $A_2$. Huang et al. suggest that a region of lipocortin I from amino acids 83–346 may be important for lipocortin activity.

SUMMARY OF THE INVENTION

In general, the invention features an isolated nucleic acid encoding an annexin XI polypeptide, the polypeptide having at least 70%, preferably at least 80%, or more preferably at least 90% homology to the amino acid sequence of bovine annexin XI type I (SEQ ID NO:2) or bovine annexin XI type II (SEQ ID NO:4). In preferred embodiments, the nucleic acid encodes a human annexin XI polypeptide.

In a related aspect, the invention features a nucleic acid having at least 70% homology to bovine annexin XI type I cDNA (SEQ ID NO:1) or bovine annexin XI type II cDNA (SEQ ID NO:3). In another aspect, the invention features a plasmid which includes a nucleic acid encoding an annexin XI polypeptide, the polypeptide having at least 70% homology to the amino acid sequence of bovine annexin XI type I (SEQ ID NO:2) or bovine annexin XI type II (SEQ ID NO:4). Preferably, the plasmid includes an expression control sequence capable of directing expression of the annexin XI polypeptide.

In a related aspect, the invention features a cell which includes a nucleic acid encoding an annexin XI polypeptide, the polypeptide having at least 70% homology to the amino acid sequence of bovine annexin XI type I (SEQ ID NO:2) or bovine annexin XI type II (SEQ ID NO:4). In preferred embodiments, the cell is a prokaryotic cell, the cell is a eukaryotic cell, and the cell is a mammalian cell.

In another aspect, the invention features annexin XI produced by expression of a nucleic acid encoding an annexin XI polypeptide, the polypeptide having at least 70% homology to the amino acid sequence of bovine annexin XI type I (SEQ ID NO:2) or bovine annexin XI type II (SEQ ID NO:4).

In a related aspect, the invention features annexin XI produced by a cell which includes a nucleic acid encoding an annexin XI polypeptide, the polypeptide having at least 70% homology to the amino acid sequence of bovine annexin XI type I (SEQ ID NO:2) or bovine annexin XI type II (SEQ ID No.4).

In another aspect, the invention features an antibody generated against all or an immunogenic portion of annexin XI, which antibody is capable of specifically forming an immune complex with annexin XI. Antibodies which specifically recognize either annexin XI type I or annexin XI type II as well as antibodies which recognize an epitope shared by type I and type II annexin XI are featured in the instant invention.

In another aspect, the invention features a substantially pure annexin XI polypeptide. In preferred embodiments, the polypeptide has at least 70%, preferably at least 80%, more preferably at least 90%, homology to the amino acid sequence of bovine annexin XI type I (SEQ ID NO: 2) or bovine annexin XI type II (SEQ ID NO: 4). In another preferred embodiment, the polypeptide is a human annexin XI polypeptide. In yet another preferred embodiment, the polypeptide has the sequence of bovine annexin XI type I (SEQ ID NO: 2) or bovine annexin XI type II (SEQ ID NO:4).

In a related aspect, the invention features a therapeutic composition which includes, in a pharmaceutically-acceptable carrier, a substantially pure annexin XI polypeptide or a coagulation inhibiting-fragment thereof.

In another related aspect, the invention includes a therapeutic composition which includes, in a pharmaceutically-acceptable carrier, a substantially pure annexin XI polypeptide, or an anti-inflammatory fragment thereof.

In another related aspect, the invention includes a therapeutic composition which includes, in a pharmaceutically-acceptable carrier, a substantially pure annexin XI polypeptide, or a phospholipase $A_2$-inhibiting fragment thereof.

The invention also features a method of detecting annexin XI in a sample of biological fluid; the method includes the steps of:
 (a) contacting the sample of biological fluid with an antibody generated against all or an immunogenic portion of annexin XI, which antibody is capable of specifically forming an immune complex with annexin XI; and
 (b) detecting immune complexes formed in step (a), formation of the immune complexes being an indication of the presence of the annexin XI.

In another aspect the invention includes a method of detecting an antibody reactive with annexin XI in a sample of biological fluid; the method includes the steps of:
 (a) contacting the sample of biological fluid with a substantially pure annexin XI polypeptide or an immunogenic fragment thereof; and
 (b) detecting immune complexes formed in step (a), formation of the immune complexes being an indication of the presence of the antibody reactive with annexin XI.

Finally, the invention features a method of reducing inflammation in a mammal involving administering to the mammal a therapeutically-effective amount of an annexin XI polypeptide or an anti-inflammatory fragment thereof in a pharmaceutically-acceptable carrier; and a method of reducing coagulation in a mammal involving administering to the mammal a therapeutically-effective amount of an annexin XI polypeptide or a coagulation-inhibiting fragment thereof in a pharmaceutically-acceptable carrier.

By "isolated" is meant that the nucleic acid is largely free of the coding sequences of those genes that, in the naturally occurring genome of the organism from which the nucleic acid is derived, directly flank the nucleic acid. Isolated nucleic acid may be genomic DNA, cDNA, chemically synthesized nucleic acid, enzymatically synthesized nucleic acid, or recombinant nucleic acid. The term includes chemically and enzymatically synthesized nucleic acid produced using a recombinant nucleic acid as a template. By "plasmid" is meant an extrachromosal DNA molecule which includes sequences that permit replication within a particular host cell. By "expression control sequence" is meant a nucleotide sequence which includes recognition sequences for factors that control expression of a protein coding sequence to which it is operably linked. Accordingly, an expression control sequence generally includes sequences for controlling both transcription and translation, for example, promoters, ribosome binding sites, repressor binding sites, and activator binding sites. "Homology" for amino acid sequences refers to the similarity between two or more amino acid sequences. The percent homology of two given proteins is usually determined using sequence analysis software (e.g., the Sequence Analysis Software Package of the Genetics Computer Group, University of Wisconsin, Madison, Wis.). Such software determines the homology of two amino acid sequences that have been aligned so as to maximize homology. Homology values are assigned to exact matches as well as certain types of substitutions.

By "substantially pure" is meant a polypeptide or protein which has been separated from components (e.g., other proteins) with which it is normally found. Typically, a protein or polypeptide of interest is substantially pure when at least 75% (preferably 85%) of the polypeptide in a sample is the protein or polypeptide of interest. By the term "capable of forming a specific immune complex" is meant an antibody does not substantially bind other molecules.

Besides substantially full-length annexin XI, the present invention provides biologically active fragments of annexin XI. As used herein, the term "fragment", as applied to annexin XI, will ordinarily be about 5 contiguous amino acids and will preferably be at least 10 or at least 20 contiguous amino acids. Such fragments may be included in larger polypeptides provided that the non-annexin XI amino acid sequences do not destroy biological activity. Multiple annexin XI fragments may be combined in a single polypeptide in any biologically active arrangement.

By "coagulation-inhibiting fragment" is meant a fragment of annexin XI which inhibits coagulation in a standard coagulation assay. Reutelingsperger et al. (*Eur. J. Biochem.* 151:625, 1985, hereby incorporated by reference) describe a modified prothrombin time test which is suitable for determining the coagulation-inhibiting activity of annexin XI and fragments thereof. Preferred fragments, when present at a concentration of 1 to 100 $\mu$M, at least double the clotting time in this assay.

By "annexin XI" is meant all alternatively spliced forms of annexin XI encoded by the same genomic locus.

By an "anti-inflammatory fragment" is meant a portion of annexin XI which is capable of reducing inflammation in any in vivo or in vitro assay. Such assays include the in vivo inflammation assay described by Parente, *Eur. J. Pharmacol.* 99:233, 1984 as well as any phospholipase $A_2$ inhibition assay, e.g., that described by Wallner et al. (U.S. Pat. No. 4,950,646, hereby incorporated by reference). In the latter assay, any fragment which inhibits phospholipase $A_2$ activity is a "phospholipase $A_2$-inhibiting fragment"; preferred fragments are those which, when present at a concentration of 1 to 100 $\mu$M, decrease phospholipase $A_2$ activity by at least 25%, and preferably by at least 50%.

DETAILED DESCRIPTION

The drawings are first briefly described.

Drawings

FIG. 1. panel A depicts the nucleotide sequence (SEQ ID NO: 1) [and] of clone pCT101. FIG. 1. panel B depicts the deduced amino acid sequence (SEQ ID NO: 2) of clone pCT101. Nucleotides are numbered from the 5'-proximal ATG, which precedes the single open reading frame. Amino acids are represented by the single letter code. The 3' end of the pCT101 clone is indicated. The four nucleotides from the end of pCT101 to the poly(A) tail were derived from the overlapping pCT20 clone;

FIG. 2 depicts a comparison between the annexin XI amino acid sequence (SEQ ID NO:4) predicted from pCT101 and the sequences of two other annexins(SEQ ID NO.13), (SEQ ID NO.14);

FIG. 3 depicts a comparison between the sequence of the SPA (panel A) (SEQ ID NO: 15)-(SEQ ID NO: 23) and EST peptides (panel B) (SEQ ID NO: 24)-(SEQ ID NO: 32) and portions several annexins;

FIG. 4 depicts the nucleotide sequence of clone pCT105 (SEQ ID NO:3);

FIG. 5 depicts the deduced amino acid sequence of clone pCT105 (SEQ ID NO:4). The bracketed sequence is present in bovine type II annexin XI, but not in bovine type I annexin XI;

FIG. 6 depicts the nucleotide sequences in the regions of the exon-intron junctions of the bovine annexin XI gene (SEQ ID NO: 33)-(SEQ ID NO: 36).

Cloning of Bovine Annexin XI

Annexin XI clones were originally isolated from a chondrocyte cDNA lambda gtll library. The largest, pCT20, had an insert approximately half the size of the predominant species detected using this cDNA as a probe on Northern blots of chondrocyte RNA. Analysis of clones indicated that internal EcoRI sites in the cDNAs were not methylated to protect against subsequent digestion by this restriction enzyme during construction of the cDNA library. Subsequently, clones corresponding to full-length mRNA were isolated from an additional chondrocyte cDNA library and a synovial cell cDNA library prepared as described below.

Isolation of Total RNA from Bovine Chondrocytes

Chondrocytes were isolated by collagenase-digestion from articular cartilage of radial carpal joints of 7 to 11 day old calves according to Towle et al. (*Biochem. Biophys. Res. Comm.* 121:134, 1984). Cells were washed and resuspended in Dulbecco's modified Eagle's medium (DMEM) with 5% fetal calf serum, and plated at $10^6$ cells per $cm^2$ in 75 $cm^2$ flasks. Synovial tissue was excised from the same radial carpal joints and cleaned of adherent connective and fat tissue. Minced tissue was incubated for 4 h in 0.08% clostridial collagenase. Partially-digested tissue was rinsed and placed in 75 $cm^2$ flasks (~2 gm per flask) in DMEM. Cultures were incubated for 3 days during which time synovial cells adhered to the culture flasks. Synovial tissue was removed, medium replaced and cultures incubated until cells appeared confluent. Confluent cells were removed from the flask by trypsin treatment (0.25%) and passaged by dividing cells from one flask into three.

Cells were cultured at 37° in a humidified atmosphere of 5% $CO_2$ 95% air. Chondrocytes and synovial cells were maintained in DMEM supplemented with ascorbate (50 $\mu$g/ml), HEPES (10 mM) pH 7.3, penicillin (100 units/ml), and streptomycin (50 $\mu$g/ml) and 10% fetal calf serum except where indicated. Chondrocytes in primary culture were incubated in DMEM containing 5% fetal calf for 24 h. Medium was replaced with serum-free DMEM and incubation continued for 24 h prior to harvesting cells for RNA extraction. Total cellular RNA was extracted from cell cultures using the guanidinium thiocyanate-phenol-chloroform procedure (Chomczynski et al., *Anal. Biochem.* 162:156, 1987).

Preparation of cDNA Libraries

Routine manipulations and analysis of nucleic acids were as described by Sambrook et al. (*Molecular Cloning: A Laboratory Manual*, Cold Spring Harbor Press, Cold Spring Harbor, N.Y., 1989). Double-stranded cDNA was synthesized using oligo(dT)12–18 as a primer on 5 $\mu$g oligo(dT)-selected chondrocyte or synovial cell RNA. Synthesis utilized Moloney murine leukemia virus reverse transcriptase, ribonuclease H and DNA polymerase I using the cDNA synthesis kit from Pharmacia (Piscataway, N.J.). [$\alpha^{32}$P] dCTP was included to monitor cDNA size. Blunt ends were generated with Klenow fragment of DNA polymerase I and the cDNAs ligated with Not I/Eco RI adapters exactly as described by Pharmacia. Adaptor-modified cDNAs were phosphorylated and size selected on Sepharose 4B (Pharmacia). Double stranded cDNAs larger than ~1.4 kb were ligated into dephosphorylated Eco RI-cut Lambda ZAP II (Stratagene, La Jolla, Calif.) Recombinant phage were packaged using the Packagene system (Promega, Madison, Wis.) and plated on XL1-Blue cells.

Identification of Annexin XI Clones

Annexin XI was initially identified by expression-library screening of a chondrocyte cDNA library in lambda gt11 using an antibody to the 57 kD latent form of the matrix metalloprotease stromelysin. The antiserum was raised by immunizing a rabbit with stromelysin purified from bovine cartilage-conditioned medium (Treadwell et al., *Arch. Biochem. Biophys.* 251:724, 1986). The predominant protein in this preparation was stromelysin, but we believe the annexin protein was present as a minor contaminant in the immunizing material.

Several cross-hybridizing partial cDNAs were identified in the lambda gt11 library and the largest (1.2 kb) was subcloned into pUC19 and M13 vectors for probe generation, restriction analysis and sequencing. Purified cDNA insert from a selected recombinant plasmid (pCT20) was labeled with [$\alpha^{32}$P] dCTP by random-primed synthesis (Feinberg et al., *Anal. Biochem.* 137:266, 1984) and used to screen un-amplified, size-selected (>1.4 kb) chondrocyte and synovial cell cDNA libraries generated in the lambda ZAP II vector (described above). Approximately 150,000 independent recombinant phage were screened, and approximately one in 10,000 hybridized with the pCT20 probe (one in 30,000 for the synovial cell library). Four cDNA clones, with inserts approximately 2300 nucleotides long, were selected for further analysis.

Analysis of Positive Clones pBluescript SK(−) phagemids were released from cross-hybridizing clones by the in vivo excision procedure and recovered by plating on XL1-Blue cells grown at 42° in the presence of ampicillin as described by Stratagene. Fragments generated by digestion of each of these cDNAs with restriction endonucleases were analyzed and subcloned into M13mp18 and M13mp19 phages. Single stranded DNAs from two clones (pCT101 and pCT105) were completely sequenced on both strands by the dideoxy chain-termination method using the primer within M13 or primers based on internal cDNA sequences. Unmodified T7 DNA polymerase was used with [in conjunction with] deaza-dGTP [was used] to resolve ambiguous sequences near the 5' end. The cDNAs within pCT101 and pCT105 were identical except for a short segment, 108 base pairs in pCT101 and 114 in pCT105, near the 5' end. Additional sequence data (approximately 200 bases in from the internal and flanking Eco RI sites) were obtained from cross-hybridizing clones.

Sequence of Annexin XI cDNAs and Predicted Proteins

FIGS. 1A and 1B shows the amino acid sequence predicted from nucleotide sequence of pCT101 cDNA. The 2300 base-pair cDNA lacks sequence corresponding to a poly(A) tail but has two potential polyadenylation signals. The two potential polyadenylation signals and putative ribosome binding sites are underlined. A poly(A) sequence terminates pCT20, an overlapping partial clone from the original lambda gt11 library corresponding to mRNA polyadenylated downstream from the somewhat unusual signal (AUUAAA) at nucleotide 2182. Clones representing mRNAs polyadenylated at the internal signal (nucleotide 1797) were not found. Furthermore, transcripts detected by Northern blot hybridization were ~2.4 kb and not ~2.2 kb as expected for mRNA utilizing the internal polyadenylation signal. Assuming a poly(A) tail of 100 to 200 nucleotides, pCT101 appears to be a complete or nearly complete copy of the mRNA. pCT125, cloned from the synovial cell library, is identical to pCT101 at the 5' end.

The most 5'-proximal ATG in pCT101 exists in a context resembling the consensus sequence for eukaryotic initiation codons (Kozak, *J. Mol. Biol.* 196:947, 1987). Nucleotides are numbered from this potential initiation codon; however, the surrounding sequence is not optimal for translation initiation, and no upstream termination codon interrupts the open reading frame extending from the 5' end of the cDNA to the TGA at position 1507. It remains possible that pCT101 and pCT105 cDNAs are incomplete and that the coding region extends beyond the 5' ends of these clones. Assuming that the 5' ATG opens the coding region, a 502 amino acid-protein with a calculated molecular mass of 54,018 daltons (including methionine) and isoelectric point 7.66 is predicted by this cDNA.

The deduced protein sequence was used to search protein data bases for similar proteins. DNA and protein sequence data were analyzed using the Genetics Computer Group Sequence Analysis Software Package. The BLAST Network Service of the National Center for Biotechnology Information was used to search the following protein databases: Protein Identification Resource release 30.0, Swiss Protein release 20.0, and translated GenBank release 70.1, update to 8/30/91. Annexin family proteins were retrieved, those most similar being annexins IV, VII, and the first tetrad of VI (61, 58, and 59% identity, respectively, within the core domain). The non-conserved amino terminal domain, however, resembles only annexin VII. This similarity is a reflection of the simple amino acid composition of these domains, which are rich in glycine, tyrosine, and proline with frequent occurrence of the tripeptide tyr-pro-gly. Alignment of annexin XI with sequences of human annexin VII (synexin) and bovine annexin IV is shown in FIG. 2. Annexin repeats in the core domain are aligned and displayed according to the scheme of Pepinsky et al. (*J. Biol. Chem.* 263:10799, 1988). The amino terminal domains of annexins XI and VII were aligned using the GAP program by the introduction of two gaps (shown as dots). The 17 amino acid consensus sequence is underlined.

Analysis of the deduced annexin XI protein revealed the presence of several characteristic motifs in addition to the annexin repeats. A potential site for asparagine-linked glycosylation exists within the amino terminal domain. However, there is no obvious signal sequence, and analysis of the protein in cell extracts using anti-peptide antibodies (see below) indicated an intracellular localization. Numerous serine and threonine residues are potential targets for phosphorylation by protein kinase C and casein kinase II. Whether these sites are actually phosphorylated has not been determined.

Characterization of Annexin XI Using Anti-Peptide Antisera

In order to identify annexin XI protein in cells, antisera were generated against two peptides predicted from sequence of pCT101 cDNA (the sequences of the peptides are double-underlined in FIG. 2).

Peptides were synthesized corresponding to a sequence in the amino terminal domain (SPA peptide: amino acids 181–193 of pCT101) and a sequence in the connecting peptide between the second and third repeat of the annexin core domain (EST peptide: amino acids 345–357 of pCT101), both non-conserved regions among annexins.

FIG. 3 illustrates a comparison of the annexin XI sequences used for synthetic peptides with other annexin proteins and shows that these peptides are derived from regions which are not conserved among annexins. To generate this figure, the annexin XI sequence was aligned using the Bestfit program with sequences of other annexins. Human lipocortins (annexins) I, III and V (Pepinsky et al. (supra), annexin VI (Sudhof et al., *Proc. Natl. Acad. U.S.A.*, 85:664, 1988), synexin (annexin VII) (Burns et al., *Proc. Natl. Acad. Sci. U.S.A.* 86:3798, 1989), and VAC-β (annexin VIII) (Hauptmann et al., *Eur. J. Biochem.* 185:63, 1989) and bovine sequences for calpactin I heavy chain (annexin II) (Kristensen et al., *Biochemistry* 25:4497, 1986) and annexin IV (Hamman et al., *Biochem. Biophys. Res. Comm.*, 156:660, 1988) are shown. Shaded residues correspond to positions of identity between the respective protein and the synthetic peptide. Asterisks indicate residues not present in the short amino terminal domains of annexins IV and V, which initiate within the range of the peptides.

The peptides were separately conjugated to KLH using MBS (Harlow et al., *Antibodies: A Laboratory Manual*, Cold Spring Harbor Press, Cold Spring, Harbor, N.Y., 1988). Cysteine residues were added to the carboxy terminus of each peptide for the purpose of coupling to carrier protein.

Rabbits were immunized according to the following protocol. Three rabbits were injected subcutaneously with each peptide-KLH conjugate (150 to 200 μg peptide) emulsified in complete Freund's adjuvant; at 21-day intervals, animals were boosted with the same antigens in incomplete Freund's adjuvant. They were bled 10 days after injection and the sera tested by direct binding enzyme-linked immunosorbent assay using a 96-well plate coated with ~50 ng free peptide per well.

Peptides were conjugated directly to Aminoethyl Bio-Gel P2 (BioRad Laboratories) (Cole et al., *Cell* 64:703, 1991). Briefly, 50 µl MBS (25 mg/ml in dimethyl formamide) was added to 10 mg resin (hydrated according to manufacturers recommendations) in 1.0 ml 10 mM $KPO_4$ pH 7.4. Resin was mixed gently for 1 h, washed with ice-cold phosphate buffer, and resuspended in 0.5 ml 10 mM HEPES (pH 6.6) containing 1 mg synthetic peptide. Conjugation proceeded for 3 h. 2-mercaptoethanol was added to a concentration of 10 mM, and after 30 min, the resin was washed with 20 mM TRIS-HCl, 150 mM NaCl, 0.02% $NaN_3$ pH 7.8 (TBS).

200 µl antiserum was diluted to 10 ml with TBST (TBS with 0.05% Tween 20) and mixed for 1 h with the respective resin conjugate. The resin was washed with five volumes of TBST. Bound antibody was eluted with 250 µl glycine HCl, 100 mM NaCl pH 2.5 and neutralized with Tris base.

The rabbit antisera were evaluated by immunoblot analysis of chondrocyte extracts and immuno-precipitation of annexin XI translated from RNA transcribed in vitro from pCT101.

For immunoblot analysis proteins which were extracted from chondrocyte monolayer cultures with EGTA and Triton X-100 were reduced and resolved (200 µg per lane) on SDS 9% polyacrylamide gels. Proteins were transferred to Immobilon and visualized by immunochemical staining using antiserum to SPA-peptide at 1:3,500 dilution as a primary antibody, the same antiserum pre-incubated 15 min with 5 µg SPA peptide, antibody affinity-purified from the same antiserum on SPA-peptide conjugated to amino-ethyl resin, antiserum to the EST-peptide at 1:1000 dilution, and the same antiserum preincubated with 5 µg of the EST-peptide, antibody affinity-purified from the same antiserum using the EST-peptide-resin conjugate or by staining with Coomassie Blue. Phosphorylase b (92 kDa) bovine serum albumin (68 kDa), ovalbumin (45 kDa), and carbonic anhydrase (30 kDa) were used to estimate molecular mass.

For protein translated in the presence of [$^{35}$S] methionine from RNA transcribed in vitro from pCT101 RNA was immunoprecipitated as described using anti-peptide antisera and resolved by SDS-PAGE. Antiserum to SPA-peptide, the same antiserum preincubated with 5 µg SPA-peptide, the same antiserum preincubated with 5 µg SPA-peptide, antiserum to EST-peptide, or the same antiserum preincubated with 5 µg EST-peptide.

Antisera prepared against the two synthetic peptides each identified a ~56 kDa protein in chondrocyte extracts. The anti-SPA serum reacted very strongly and quite specifically with this protein on immunoblots, while un-purified anti-EST serum recognized multiple proteins in addition to the ~56 kDa protein. The protein translated from RNA transcribed in vitro from pCT101 co-migrated on SDS-page with the ~56 kDa immunoreactive chondrocyte protein and was immunoprecipitated by each antiserum. Furthermore, preincubation of each antiserum with the corresponding free peptide prevented both immunoprecipitation and detection of protein on immunoblots. These results demonstrate the specificity of the anti-peptide antisera and identify a chondrocyte protein, ~56,000 molecular weight, as annexin XI.

Tissue Distribution of Annexin XI

Northern blot analysis of chondrocyte RNA demonstrated that pCT101 cDNA probes hybridized to produce a single major signal slightly above 2.4 kb. (A minor signal occasionally visible near the position of 28 S ribosomal RNA probably represents unprocessed or partially-processed transcript, since it was not evident in oligo-dT-selected RNA.) Annexin XI transcripts were present at comparable levels in a variety of specialized bovine cells including chondrocytes, synovial cells at third passage, SBAC adrenal cortical cells, and MDBK kidney epithelial cells. Annexin XI was identified among proteins extracted from bovine cells using anti-peptide antibodies on immunoblots. The ~56 kDa protein was present in approximately equal relative abundance in EGTA-Triton extracts prepared from each cell type. Protocols for Northern blot analysis and immunoblot analysis are described below.

In vitro Transcription and Translation

Annexin XI recombinant plasmid PCT10 was linearized by digestion with Hind III, which cleaves within the multiple cloning site downstream from the cDNA insert. One µg plasmid was transcribed using T3 RNA polymerase and the Pharmacia in vitro transcription kit following the recommendations of the supplier for the 7-methyl guanosine capping protocol and DNAase I digestion. Reaction products were extracted with phenol and chloroform, precipitated with sodium acetate and ethanol, and dissolved in 20 µl water. One µl of RNA was translated 60 min at 37° in a 10 µl reaction using micrococcal nuclease-treated rabbit reticulocyte lysate (Promega) supplemented with [$^{35}$S] methionine.

Preparation of Cell Extracts

Chondrocytes and cells from established bovine cell lines were placed in 75 $cm^2$ flasks and cultured for 3 days, medium being changed 24 h before extraction of cell proteins. Protein extraction from confluent monolayers was performed on ice. Cells were washed twice with serum-free minimal Eagle's medium. Five ml buffer A (TBS with 10 mM EGTA) was added to each flask. The protein in the "EGTA extract" was recovered after 5 min. Five ml buffer A containing 0.5 Triton X-100 was added to each flask, and after 5 min the "EGTA-Triton" extract was recovered. Protein solutions were stored in aliquots at −40° prior to immunoblot analysis.

Immunoprecipitation

Translation products were diluted to 100 µl with SDS-PAGE sample buffer containing 1% 2-mercaptoethanol and boiled for 3 min. Samples were centrifuged 12,000 g 5 min and the supernatants diluted with four volumes of TBS containing 1% Triton x-100, 0.5% Tween 20, 10 mM EDTA, 1 µg/ml aprotinin. Antiserum (2 µl) was added, mixtures were incubated for 1 h, and the immune complexes were captured on protein A Sepharose. Beads were washed with the same buffer. Four bovine cell lines were obtained as frozen cells from American Type Culture Collection, Rockville, Md. These cell lines are described by the supplier as follows: SBAC is a normal endocrine cell line derived from adrenal cortex and responsive to adrenocorticotropic hormone. CPAE are normal endothelial cells derived from pulmonary artery and possessing angiotensin-converting enzyme activity. MDBK are hypo-diploid kidney cells of epithelial-like morphology. EBTr cells are normal and hypo-diploid fibroblast-like cells derived from embryonic trachea.

Frozen cells were thawed and diluted to $3 \times 10^5$ cells/ml in minimum essential Eagle's medium with non-essential amino acids and Earle's balanced salt solution. Medium was supplemented with heat inactivated newborn calf serum at 10% (20% for CPAE cells). Cells were cultured in 75 $cm^2$ flasks, with media changes at three-day intervals, until confluent. Cells were passaged as for synovial cells.

Isolation of RNA

Synovial cells (third passage) and cells from bovine cell lines were incubated three days after sub-culturing, medium being replaced 24 h before extraction of RNA for Northern blot analysis.

Northern blot analysis

Ten to 15 µg total RNA was resolved on 1% agarose formaldehyde gels and transferred to nitrocellulose by capillary blotting. Blots were baked under vacuum and prehybridized in 5× SSPE (1× is 180 mM NaCl, 10 mM NaPO$_4$, 1 mM EDTA, pH 7.7), 50% formamide, 1% N-lauryl sarcosine, 1× Denhardt's (Ficoll, polyvinyl pyrrolidone, and bovine serum albumin each at 0.02%), and 100 µg/ml boiled, sonicated salmon sperm DNA. cDNA inserts of plasmids were purified on low gel-temperature agarose and labeled with [$\alpha^{32}$p]dCTP by random primed synthesis (Feinberg et al., supra). Probes were denatured by boiling and added at 10 ng/ml to the same buffer used for hybridization. Hybridization was for 18 h at 42°. Blots were washed at 65° with 0.2× SSPE 1% N lauryl sarcosine. Nitrocellulose was exposed to X-ray film with intensifying screen at −40° C. for 1–3 days.

SDS polyacrylamide gel electrophoresis

Proteins present in acetone- or immuno-precipitates, were solubilized by boiling 3 min in 25 µl SDS sample buffer containing 2% 2-mercaptoethanol. Proteins were resolved on 9% polyacrylamide gels.

Immunoblot analysis

Gels were equilibrated with 20 mM Tris base, 150 mM glycine, 15% methanol and the resolved proteins electrophoretically transferred to Immobilon. Membranes were blocked by incubation for 1 hr at 37° in 3% gelatin prepared in TBS. Membranes were incubated for 1 hr with antisera or affinity-purified anti-peptide antibodies (10 to 50 ng per ml in TBST 1% gelatin), washed with TBST, and incubated 1 hr with 1:7500 dilution of alkaline phosphatase-conjugated goat anti-rabbit IgG (Promega). The blots were washed with TBST and developed with nitroblue tetrazolium and 5-bromo-4-chloro-3-indolyl phosphate as the chromogenic substrate.

Modification of Annexin XI

There is a potential site of N-linked glycosylation within the amino terminal domain. To determine whether annexin XI protein was glycosylated on asparagine, protein extracted from chondrocytes by EGTA and Triton X-100 was incubated with N-glycanase and then subjected to immunoblot analysis using anti-peptide antibodies. Enzymatic treatment did not alter the mobility of the immunoreactive species on SDS-PAGE. Furthermore, annexin XI was undetectable in chondrocyte culture medium or the EGTA-extract of live cells but was extracted by EGTA in the absence of detergent from hypotonically-lysed chondrocytes (results not shown). These observations suggest that annexin XI was predominantly intracellular.

Characterization of Alternatively Spliced Forms of Annexin XI

Described below are a series of experiments demonstrating the existence of alternatively spliced annexin XI transcripts capable of encoding proteins which differ near the amino terminus. Clones PCT101 and pCT105 represent these distinct forms of bovine annexin XI (type I and type II respectively).

The pCT105 and pCT101 cDNAs were identical except for a short segment, 109 bp in pCT101 and 115 bp in pCT105, where the two sequences were completely different; this sequence divergence within the pCT101 coding regions did not disrupt the reading frame. Translation of the two species of mRNA would result in two kinds of annexin XI proteins differing at the amino terminal ends.

FIG. 4 depicts the partial nucleotide (SEQ ID NO: 3) of the pCT105 cDNA clone; FIG. 5 depicts the deduced amino acid sequence (SEQ ID NO: 4) of the pCT105 cDNA clone. The 5' proximal ATG common to both annexin XI cDNAs approximates the consensus initiation context defined by Kozak (*J. Mol. Biol.* 196:947, 1987). This is most likely used to initiate the type I protein, since alternative sites would result in a protein substantially different in size from the ~56 kDa annexin XI identified by immunoblotting using anti-peptide antisera. However, three additional in frame methionine codons exist within the variant region of the type II mRNA, and one conforms even more closely to the consensus initiation sequence. Should this alternative site be utilized for translation initiation, the product would be a ~49 kD polypeptide. This polypeptide would include a stretch of twelve neutral, mostly hydrophobic residues near the amino terminus. The sequence weakly conforms to the consensus signal sequence defined by von Heijne (*J. Mol. Biol.* 184:99, 1985), suggesting that at least some annexin XI may be secreted by the conventional route to function extracellularly.

The antibodies described above would recognize both forms of annexin XI and therefore cannot be used to determine whether both transcripts are translated. The two proteins could be distinguished by size if the internal methionine codon initiated translation of the type II protein. Immunoblot analysis of bovine chondrocyte extracts using anti-peptide antisera described above identified a 56 kDa protein. A minor 50 kDa protein visible on a blot from an over-loaded (500 µg protein) SDS polyacrylamide gel may represent type II protein or a type I degradation product. Anti-peptide antisera based on the sequence predicted from the variant regions of pCT101 and pCT105 can likely be used for analysis of the two annexin XI isoforms.

Expression of Annexin XI Transcripts

Type I and type II specific labeled oligonucleotide probes were used in an attempt to identify the two annexin XI transcripts by Northern blot analysis. Type I transcripts were readily visualized; however, type II transcripts were not observed, even on blots of 20 µg polyA$^+$ chondrocyte RNA. Accordingly, type II mRNA, if present, is expressed at much lower levels than type I mRNA in this cell type.

In order to verify that the pCT105 clone represented an annexin XI transcript, cDNAs reverse transcribed from chondrocyte or MDBK cell RNA were analyzed by polymerase chain reaction (PCR) amplification. The strategy was to co-amplify cDNAs derived from the two classes of mRNA using pairs of primers that span the region of sequence divergence identified in the pCT101 and pCT105 clones. To increase the specificity of PCR, we carried out two sequential sets of 28- cycle reactions using different pairs of specific primers.

The following oligonucleotides were used for PCR analysis:

A: AGATCTAGCCATGAGCTCCCCAGGCTACC (SEQ ID NO:5) common to pCT101 and pCT105

B: CCCGCAG<u>GTGGCTAGC</u>CACCAGGT (SEQ ID NO:6) common to PCT101 and pCT105

C: AGGTTTGGCACGTT<u>GGATCC</u>TCCAA (SEQ ID NO:7) common to pCT101 and pCT105 (antisense)

D: CAACTATGCAGGGCAGTTCAACCA (SEQ ID NO:8) pCT101 specific

E: CCACATTATCCAGCCCAATGGGAGGCA (SEQ ID NO:9) pCT101 specific (antisense)

F: AGCTGGAAAGCCACGCTGGAGGCC (SEQ ID NO:10) pCT105 specific

G: TGGACAGGGCTGTTTCTGACGGGCC (SEQ ID NO:11) pCT105 specific

H: CAAGTAGCACAGCAGCTAGCATCATGGC (SEQ ID NO:12) pCT105 specific (antisense)

Restriction sites introduced to facilitate cloning of PCR products are underlined. All oligonucleotides were purchased from Oligos Etc. (Medford, Oreg.). Some of these oligonucleotides were also used as sequencing primers and hybridization probes for anlysis of PCR products and clones.

PCR amplifications were carried out in a Biosycler thermal cycler (Bios Corp., New Haven, Conn.). Reaction mixtures (100 μl) contained 100 pmol of each primer, 200 μM each of the four deoxynucleoside triphosphates, 5 units Taq polymerase (Promega, Madison, Wis.), and template; the buffer supplied by Promega was optimized with respect to $Mg^{+2}$ concentration for each primer pair using cDNA templates.

Aliquots of PCR products, untreated or digested with restriction endonucleases that cut within the variant regions of PCT101 and pCT105, were resolved by agarose gel electrophoresis and transferred to Biotrans nylon membranes (ICN, Irvine, Calif.). Oligonucleotides designed from the variant region sequences (D–H) were labeled at the 5'-ends using T4 polynucleotide kinase for use as hybridization probes.

Cell culture and RNA extraction were as described above. Complimentary DNA was synthesized in a 15 μl reaction using Moloney murine leukemia virus reverse transcriptase and the first strand cDNA synthesis kit from Pharmacia (Piscataway, N.J.). The supplied NotI-oligo d(T)18 oligonucleotide served to prime synthesis on 3 μg total RNA from chondrocytes or MDBK (bovine kidney epithelial) cells. The resulting single strand cDNAs (5 μl) were templates for PCR using primers (A and C) that span the segment of sequence divergence between the pCT101 and pCT105 cDNA clones. Amplification was for 28 cycles, each consisting of a 30 sec denaturation step (94°), a 30- sec annealing (56°) step, and a 30 sec extension (72°) step. One μl of each product was further amplified through 28- cycles (same profile) using primers B and C. In order to specifically amplify the low abundance type II mRNA, pairs of primers, one specific to pCT105 and one common to both cDNAs (A and H or F and C), were used to re-amplify the product of the first PCR (5 μl). DNA synthesized in the reactions was analyzed by restriction endonuclease digestion and Southern blot hybridization.

The amplified products and restriction fragments visualized by autoradiography were the sizes expected from cDNA sequences of pCT101 and pCT105. These data provide strong evidence for the presence of both classes of annexin XI transcripts in MDBK cells and chondrocytes. Because the efficiency of reverse transcriptase varies with the template, this PCR assay can not be considered quantitative. However, these results taken with the fact that type II species could not be detected on Northern blots, suggest that the type II transcript is a minor mRNA in these cells.

Alternative Splicing Generates Two Classes of Annexin XI mRNA (Type I and Type II).

Alternative splicing of identical annexin XI primary transcripts could generate the mRNA diversity indicated by the pCT101 and pCT105 cDNA clones. In order to determine whether the two variant sequences are encoded by the same region of the genome, various pair-wise combinations of primers corresponding to the divergent and common regions of pCT101 and pCT105 were used to amplify bovine genomic DNA by PCR. PCR products were digested with restriction endonucleases specific to each putative exon, and the resulting DNA fragments were resolved by agarose gel electrophoresis were analyzed by Southern blot hybridization.

The first amplification reaction contained 100 pmol each of 5' primer A and 3' primer C with 10 μg bovine genomic DNA (Clonetech, Palo Alto, Calif.) as template. Three cycles of 1 min denaturation (94°), 30 sec annealing (56°), 2.5 min extension (72°) were followed by 25 cycles with the same parameters except that the denaturation time was 30 sec. The product (5 μl) of the first PCR amplification was used as the template in a second amplification (same parameters) employing 100 pmol each of primers B and C.

The major product of the second amplification reaction, ~2.5 kb, was cloned as two restriction fragments into pGEM3z (Promega, Madison, Wis.). Aliquots of the reaction mixture containing 200 ng of the 2.5 kb DNA were digested with NheI for cloning into XbaI-digested pGEM3z or with NheI plus BamHI for ligation into XbaI and BamHI digested vector. Restriction digests were heat-inactivated, passed over Chromaspin 400 (Clontech, Palo Alto, Calif.), ethanol precipitated and ligated with appropriately digested vector. Competent DH5α cells (BRL, Bethesda, Md.) were transformed, and transformants were selected on ampicillin plates. Positive colonies were identified by standard hybridization techniques using oligonucleotides labeled at the 5' end.

These experiments established that: 1) a genomic fragment ~2.5 kb was amplified by primers designed from sequence spanning the variant regions of pCT101 and pCT105; 2) restriction endonucleases specific to each of the variant regions cleaved the PCR products, and 3) the deduced order of putative exons in the gene is 5' common, type II-specific, type I-specific, and 3' common.

Primers bracketing the variant segment of pCT101 and pCT105 cDNAs were used to amplify the region of the annexin XI gene containing the two putative alternatively spliced exons. The ~2.5 kb PCR product was cloned, and the cloned DNA was sequenced. FIG. 6 depicts the nucleotide sequences in the regions of exon-intron junctions as determined by sequencing PCR clones. Exons and introns were identified by comparison of the cDNA sequences with that of the cloned genomic PCR product.

This analysis confirms that the type I-specific and type II-specific sequences are arranged as neighboring discrete exons in the bovine genome. The exon/intron junctions are in good agreement with consensus sequences for these regions (Mount, *Nucl. Acids Res.* 10:459, 1982). Split codons, G at the 3' boundary of the 5' common exon spliced to GU of the type I-specific and type II-specific exons, encode the glycine residue that precedes the divergence of the two annexin XI deduced proteins. The 3' borders of these exons separate (rather than split) codons, as does the 5' border of the 3' common exon. Thus, either of the two specific exons serve as the adaptor necessary to join the 5' and 3' common exons without shifting the reading frame.

The primary transcript of a single annexin XI gene can apparently be processed into either of two different mRNAs, each having one of two specific exons. Such alternative splicing, the mutually-exclusive utilization of exons in the processed RNA, in most cases has evolved from an exon duplication event (Breitbart et al., *Ann. Rev. Biochem.* 56:467, 1987).

While we have described alternative RNA splicing as a means of generating two annexin XI gene products our experiments do not exhaust the possibilities for additional splicing variants. Alternative splicing of annexin XI may be regulated. If so, identification of conditions associated with elevated expression of the type II species might provide a clue to the function(s) of this novel annexin. Such conditions would also facilitate an examination of the biosynthetic processing of the two types of protein.

Cloning of Human Annexin XI

Human annexin XI can be easily cloned from an appropriate cDNA library using bovine annexin XI cDNA as a probe. Suitable cDNA libraries include: human monocyte, U937 cells, phorbol myristate-stimulated, human adrenal, and human kidney (Clontech, Palo Alto, Calif.). Purified cDNA insert from pCT101 or pCT105 can be labeled with [$\alpha^{32}$P]dNTP by random-primed synthesis (Feinberg et al., supra) and used to screen an appropriate human cDNA library. Positive clones can be sequenced and should have >80% homology to bovine annexin XI.

In an alternative approach, oligonucleotide probes, designed based on the sequence of bovine annexin XI (SEQ ID NO:1), can be used to isolate a bovine annexin XI clone from a bovine chondrocyte cDNA library. This bovine annexin XI clone can be used in place of pCT101 or pCT105 cDNA to isolate human annexin XI. Oligonucleotide probes, designed based on the sequence of bovine annexin XI (SEQ ID NO:1) may be used to directly screen a human cDNA library as described above. Those skilled in the art will recognize that the probes should be selected from regions of bovine annexin XI that are not significantly homologous to other annexins (e.g., annexin VII or annexin IV).

In another alternative approach, the oligonucleotide primers described above (SEQ ID NO:5 and SEQ ID NO: 7) can be used to amplify a human annexin XI fragment from human genomic DNA (e.g., available from Clontech, Palo Alto, Calif.) by polymerase chain reaction. The amplified fragment is then $^{32}$P-labeled, e.g., by the random-primed synthesis method of Feinberg et al.(supra) and used to probe a human genomic (e.g., a human leukocyte) DNA library in order to isolate the full-length human annexin XI clone.

Biologically Active Polypeptides

Polypeptide fragments of annexin XI can be generated by proteolysis. Limited or complete proteolysis by elastase or proteinase K can be used to generate fragments of varied length since they hydrolyze peptide bonds rather non-specifically. Plasmin and other proteases which hydrolyze peptide bonds in a more structure and sequence dependent manner may also be used to generate useful polypeptide fragments. Polypeptide fragments generated by proteolytic digestion can be isolated by column chromatography. Fragments may also be produced by genetic engineering techniques or by standard techniques of chemical peptide synthesis.

Desirable polypeptide fragments are those which inhibit inflammation. Such fragments may, e.g., inhibit phospholipase $A_2$ activity, as measured, e.g., using the assay described by Wallner et al. (U.S. Pat. No. 4,950,646 or they may inhibit in vivo inflammation as assayed by the method of Parente (*Eur. J. Pharmacol.* 99:233, 1984; hereby incorporated by reference).

Other desirable polypeptide fragments inhibit coagulation. Coagulation inhibiting activity can be measured using the assay described by Reutelingsperger et al. (*Eur. J. Biochem.* 151:625, 1985).

Use

Because annexins inhibit phospholipase $A_2$ activity, annexin XI and polypeptide fragments thereof will be useful for reducing inflammation associated with arthritis, allergies, dermatologic disorders, ophthalmic disorders, and collagen diseases.

In addition, since annexins have anti-coagulant activity, annexin XI and polypeptide fragments thereof will be useful for inhibiting coagulation.

The polypeptides of the invention can be administered in an effective amount either alone or in combination with a pharmaceutically acceptable carrier or diluent. The polypeptides and compositions can be administered alone or in combination with other therapeutic agents. If appropriate, multiple therapeutic annexin XI peptides (e.g., multiple biologically-active annexin XI fragments) may be administered either simultaneously or sequentially.

The polypeptides and compositions of the invention may be administered by any convenient means, e.g., intravenously, intra-articularly, orally, intramuscularly, or intranasally.

Annexin XI and immunogenic polypeptide fragments thereof can be used to screen for autoantibodies associated with a variety of pathological states. Similarly, antibodies raised against annexin XI and immunogenic polypeptide fragments thereof can be used to measure annexin XI levels in synovial fluid for the purpose of detecting pathologic conditions. Such antibodies can be used in any standard format such as a radioimmunoassay, an ELISA assay, or a Western blot.

Increased levels of anti-annexin XI autoantibodies may be present in patients treated with corticosteroids (e.g., patients receiving corticosteroids as a treatment for inflammatory diseases such as rheumatoid arthritis). It has been proposed that autoantibodies against another annexin (lipocortin-1) are responsible for "steroid resistance" in patients receiving prolonged treatment with corticosteroids (Goulding et al., *Annals Rheum. Diseases* 48:843, 1989). Accordingly, monitoring of anti-annexin XI autoantibodies may provide a means by which to monitor corticosteroid treatment. Increased levels of anti-annexin XI autoantibodies may also be present in patients with inflammatory diseases such as systemic lupus erythematosus. Detection of such autoantibodies using annexin XI may be useful in diagnosis of inflammatory diseases. Annexin XI can be used in a radioimmunoassay, an ELISA assay, a Western blot, or any other standard format immunoassay to measure anti-annexin autoantibody levels in human sera or synovial fluid. Such assays might employ annexin XI and detectably labeled rabbit antihuman IgM or rabbit antihuman IgG antibody.

Anti-annexin XI antibodies can be used in a standard immunoassay to measure annexin XI levels in human sera of synovial fluid. Altered annexin XI levels may be associated with a number of inflammatory diseases such as arthritis.

Other Embodiments

Antibodies capable of specifically forming an immune complex with annexin XI can be produced by standard techniques (see Harlow et al, supra) using intact annexin XI or immunogenic fragments thereof. Annexin XI fragments can be generated by digestion of annexin XI with proteases or by synthesizing peptides chemically.

SEQUENCE LISTING (1) GENERAL INFORMATION:

(iii) NUMBER OF SEQUENCES:    36

(2) INFORMATION FOR SEQ ID NO:    1:

(i) SEQUENCE CHARACTERISTICS:
      (A) LENGTH:           2305
      (B) TYPE:             nucleic acid
      (C) STRANDEDNESS:  single
      (D) TOPOLOGY:         linear (xi) SEQUENCE DESCRIPTION: SEQ ID NO: 1:

| | |
|---|---:|
| TCGGAGGTGC TGCGCCTGGG ACGCCCGGAG AGAGAGCTGC TTCTGCCCGC | 50 |
| GTCCCACGTC TCCCCTCGCG ACTCCCCACT GCCCCGTGGC CAGATCTAGC | 100 |
| C | 101 |
| ATG AGC TAC CCA GGC TAC CCC CCG CCC GCA GGT GGC TAC CCA CCA | 146 |
| GGT GCA CCA GGT GGC GGT GCC TGG GGA GGT GCT GGC TAC CCG CCA | 191 |
| CCC ACC ATG CCT CCC ATT GGG CTG GAT AAT GTG GCC AAC TAT GCA | 236 |
| GGG CAG TTC AAC CAG GAC TAC CTC TCA GGA GTG GCG GCC AAC ATG | 281 |
| TCC GGG ACG TTT GGA GGA GCC AAC GTG CCA AAC CTG TAC CCG GGG | 326 |
| GCC CCT GGG GGT GGT TAC CCC CCA GTT CCC CCG GGG GGG TTC GGG | 371 |
| CAG CCC CCT CCC GCC CAG CAG CCT GTT CCT TCG TAT GGA ATG TAC | 416 |
| CCG CCC CCT GGA GGA AAC CCC ACC TCC GGG ATG CCT TCA TAT CCG | 461 |
| CCA TAC CCA GGG GCC CCT GTG CCA GGC CAG CCC ATG TTG CCC CCT | 506 |
| GGA CAG CAG CCC CCA GGG GTC TAC CCT GGA CAG CCG CCC ATG ACC | 551 |
| TAC CCT GGA CAG TCA CCA GTG CCA CCT CCT GGG CAG CAG CCA GTG | 596 |
| CCA AGC TAT CCA GGG TAC TCA GGT TCT GGG ACT GTC ACC CCT GCC | 641 |
| GTG TCC CCC GCT CAG TTT GGA AAC CGA GGC ACC ATC ACA GAT GCA | 686 |
| TCT GGC TTT GAC CCC CTG CGA GAT GCT GAA GTC CTG CGG AAG GCC | 731 |
| ATG AAG GGC TTT GGG ACT GAC GAG CAG GCC ATC ATT GAC TGC CTG | 776 |
| GGT AGT CGC TCC AAC AAG CAA CGA CAG CAG ATC CTC CTG TCG TTC | 821 |
| AAG ACA GCA TAT GGG AAG GAT TTG ATC AAA GAT CTG AAA TCT GAA | 866 |
| CTG TCA GGA AAC TTT GAG AAG ACA ATC TTG GCC CTG ATG AAG ACC | 911 |
| CCT GTC CTC TTT GAC GCT TAT GAG ATA AAG GAA GCT ATC AAG GGG | 956 |
| GCG GGC ACT GAT GAA GCC TGC CTG ATC GAG ATC CTG GCC TCC CGC | 1001 |
| AGC AAC GAG CAC ATC CGG GAG CTG AAC AGA GTC TAC AAG ACA GAA | 1046 |
| TTC AAA AAG ACC CTG GAG GAG GCC ATT CGG AGC GAC ACT TCA GGG | 1091 |
| CAC TTC AGG CGG CTC CTC ATC TCT CTC TCT CAG GGA AAC CGG GAT | 1136 |
| GAA AGC ACA AAC GTG GAC ATG ACC CTT GTC CAG AGA GAT GTG CAG | 1181 |
| GAG CTC TAT GCA GCT GGG GAG AAC CGC CTG GGA ACA GAT GAG TCC | 1226 |
| AAG TTC AAT GCG ATT CTG TGC TCC CGG AGC CGG GCC CAC CTG GTG | 1271 |
| GCA GTT TTT AAC GAG TAT CAG AGG ATG ACA GGA CGT GAC ATT GAG | 1316 |
| AAG AGC ATC TGC CGG GAG ATG TCC GGG GAC CTG GAG CAG GGC ATG | 1361 |

```
CTG GCT GTG GTG AAA TGT CTT AAG AAT ACC CCA GCC TTC TTT GCT        1406

GAA AGG CTC AAC AAG GCC ATG AGG GGA GCC GGA ACC AAA GAC CGG        1451

ACC CTG ATC CGC ATC ATG GTG TCT CGC AGC GAG ATC GAC CTC CTG        1496

GAC ATC AGA GCA GAG TAT AAG CGG CTG TAT GGC AAG TCG CTG TAC        1541

CAC GAC ATC ACG GGA GAC ACT TCA GGG GAT TAC CGG AAG ATT CTG        1586

CTG AAG ATC TGT GGT GGC AAT GAC TGAGCAGTG                          1619

GCTGGTGGGT CACTTCTGTC CACCTGCTGG CAACAGCAAT GCCAGGAAAA             1669

GGCCAAAAGA ACGTTTGTCT GTTTCTAACA AATCTACAAA GTAGCCCCCA             1719

GGTGTCACAG TTCAGACCAA CTGTAGAGCC TTGGCCCCAT CTCCTCCCCC             1769

GCCCTCGATC CGTGCATTGT GCTTGTGCCC GAGAACCTAG TCAGTCTCGA             1819

ACTCTCTCAG GACGCCTCCT CCCCATCCCG ACCCCTCACA GCCTCTTGCA             1869

GCTTAAAGTA GATGTTTTGT TCCTGAAAAA TAAACTCTGG CTTCCTCTAG             1919

TCATGTAGTT TTGTATGTTT AGAGGTTTTT TTTTTTTTTT TAATAATTAG             1969

TTGCAGACAG TTGCATACAC ATCTTTGCTG CATACAAAGT TTGGATAAAA             2019

GAGGTGGGGG GTTGGAGTGC CATGTCTTCA CTGAGGAGTA AAAGGAAAAC             2069

TTTCAGGATA GACTCTGCAT CTGGTGAAAA TGTGTCATGA GCTTTGTTGT             2119

TGCCAAACTC ACTCCTTTTT AGAAAAGAAA AGGCCAGAAA GTCATCTGTT             2169

CTTTCTTCTA CACAAACCAC AAGAACAAAG CCAGCTCCCT GCCAGTGACA             2219

GGGCTTCTTG TAATTGAGAA TGTGCCTTAA CCTGAATGTT GATGGCCAAA             2269

TGCTGTTTCC AAATTAAAGT CTGCCAGCTC TGAAAA                            2305

(2) INFORMATION FOR SEQ ID NO:    2:

(i) SEQUENCE CHARACTERISTICS:
        (A) LENGTH:              503
        (B) TYPE:                amino acid
        (D) TOPOLOGY: Not Relevant (xi) SEQUENCE DESCRIPTION: SEQ ID NO: 2:

Met Ser Tyr Pro Gly Tyr Pro Pro Pro Ala Gly Gly Tyr Pro Pro
                  5                  10                  15

Gly Ala Pro Gly Gly Gly Ala Trp Gly Gly Ala Gly Tyr Pro Pro
                 20                  25                  30

Pro Thr Met Pro Pro Ile Gly Leu Asp Asn Val Ala Asn Tyr Ala
                 35                  40                  45

Gly Gln Phe Asn Gln Asp Tyr Leu Ser Gly Val Ala Ala Asn Met
                 50                  55                  60

Ser Gly Thr Phe Gly Gly Ala Asn Val Pro Asn Leu Tyr Pro Gly
                 65                  70                  75

Ala Pro Gly Gly Gly Tyr Pro Pro Val Pro Pro Gly Gly Phe Gly
                 80                  85                  90

Gln Pro Pro Pro Ala Gln Gln Pro Val Pro Ser Tyr Gly Met Tyr
                 95                 100                 105

Pro Pro Pro Gly Gly Asn Pro Thr Ser Gly Met Pro Ser Tyr Pro
                110                 115                 120

Pro Tyr Pro Gly Ala Pro Val Pro Gly Gln Pro Met Leu Pro Pro
                125                 130                 135

Gly Gln Gln Pro Pro Gly Val Tyr Pro Gly Gln Pro Pro Met Thr
```

```
                140                 145                 150
Tyr Pro Gly Gln Ser Pro Val Pro Pro Gly Gln Gln Pro Val
                155                 160                 165

Pro Ser Tyr Pro Gly Tyr Ser Gly Ser Gly Thr Val Thr Pro Ala
                170                 175                 180

Val Ser Pro Ala Gln Phe Gly Asn Arg Gly Thr Ile Thr Asp Ala
                185                 190                 195

Ser Gly Phe Asp Pro Leu Arg Asp Ala Glu Val Leu Arg Lys Ala
                200                 205                 210

Met Lys Gly Phe Gly Thr Asp Glu Gln Ala Ile Ile Asp Cys Leu
                215                 220                 225

Gly Ser Arg Ser Asn Lys Gln Arg Gln Gln Ile Leu Leu Ser Phe
                230                 235                 240

Lys Thr Ala Tyr Gly Lys Asp Leu Ile Lys Asp Leu Lys Ser Glu
                245                 250                 255

Leu Ser Gly Asn Phe Glu Lys Thr Ile Leu Ala Leu Met Lys Thr
                260                 265                 270

Pro Val Leu Phe Asp Ala Tyr Glu Ile Lys Glu Ala Ile Lys Gly
                275                 280                 285

Ala Gly Thr Asp Glu Ala Cys Leu Ile Glu Ile Leu Ala Ser Arg
                290                 295                 300

Ser Asn Glu His Ile Arg Glu Leu Asn Arg Val Tyr Lys Thr Glu
                305                 310                 315

Phe Lys Lys Thr Leu Glu Glu Ala Ile Arg Ser Asp Thr Ser Gly
                320                 325                 330

His Phe Gln Arg Leu Leu Ile Ser Leu Ser Gln Gly Asn Arg Asp
                335                 340                 345

Glu Ser Thr Asn Val Asp Met Thr Leu Val Gln Arg Asp Val Gln
                350                 355                 360

Glu Leu Tyr Ala Ala Gly Glu Asn Arg Leu Gly Thr Asp Glu Ser
                365                 370                 375

Lys Phe Asn Ala Ile Leu Cys Ser Arg Ser Arg Ala His Leu Val
                380                 385                 390

Ala Val Phe Asn Glu Tyr Gln Arg Met Thr Gly Arg Asp Ile Glu
                395                 400                 405

Lys Ser Ile Cys Arg Glu Met Ser Gly Asp Leu Glu Gln Gly Met
                410                 415                 420

Leu Ala Val Val Lys Cys Leu Lys Asn Thr Pro Ala Phe Phe Ala
                425                 430                 435

Glu Arg Leu Asn Lys Ala Met Arg Gly Ala Gly Thr Lys Asp Arg
                440                 445                 450

Thr Leu Ile Arg Ile Met Val Ser Arg Ser Glu Ile Asp Leu Leu
                455                 460                 465

Asp Ile Arg Ala Glu Tyr Lys Arg Leu Tyr Gly Lys Ser Leu Tyr
                470                 475                 480

His Asp Ile Thr Gly Asp Thr Ser Gly Asp Tyr Arg Lys Ile Leu
                485                 490                 495

Leu Lys Ile Cys Gly Gly Asn Asp
                500
```

(2) INFORMATION FOR SEQ ID NO: 3:

(i) SEQUENCE CHARACTERISTICS:
        (A) LENGTH:             2311

```
        (B) TYPE:            nucleic acid
        (C) STRANDEDNESS:    single
        (D) TOPOLOGY:        linear (xi) SEQUENCE DESCRIPTION: SEQ ID NO: 3:

TCGGAGGTGC TGCGCCTGGG ACGCCCGGAG AGAGAGCTGC TTCTGCCCGC          50

GTCCCACGTC TCCCCTCGCG ACTCCCCACT GCCCCGTGGC CAGATCTAGC         100

CATGAGCTAC CCAGGCTACC CCCCGCCCGC AGGTGGCTAC CCACCAGGTG         150

CACCAGGTGT CCCGGAGCTG GAAAGCCACG CTGGAGGCCC CCAGGGCCTT         200

TTCGCTGCCA TGGACAGGGC TGTTTCTGAC GGGCCAGCCA TGATGCTAGC         250

TGCTGTGCTA CTTGTGAGGG CTACGGCGGC CAACATGTCC GGGACGTTTG         300

GAGGAGCCAA CGTGCCAAAC CTGTACCCGG GGGCCCCTGG GGGTGGTTAC         350

CCCCCAGTTC CCCCGGGGGG GTTCGGGCAG CCCCCTCCCG CCCAGCAGCC         400

TGTTCCTTCG TATGGAATGT ACCCGCCCCC TGGAGGAAAC CCCACCTCCG         450

GGATGCCTTC ATATCCGCCA TACCCAGGGG CCCCTGTGCC AGGCCAGCCC         500

ATGTTGCCCC CTGGACAGCA GCCCCCAGGG GTCTACCCTG ACAGCCGCC          550

CATGACCTAC CCTGGACAGT CACCAGTGCC ACCTCCTGGG CAGCAGCCAG         600

TGCCAAGCTA TCCAGGGTAC TCAGGTTCTG GGACTGTCAC CCCTGCCGTG         650

TCCCCCGCTC AGTTTGGAAA CCGAGGCACC ATCACAGATG CATCTGGCTT         700

TGACCCCCTG CGAGATGCTG AAGTCCTGCG GAAGGCCATG AAGGGCTTTG         750

GGACTGACGA GCAGGCCATC ATTGACTGCC TGGGTAGTCG CTCCAACAAG         800

CAACGACAGC AGATCCTCCT GTCGTTCAAG ACAGCATATG GGAAGGATTT         850

GATCAAAGAT CTGAAATCTG AACTGTCAGG AAACTTTGAG AAGACAATCT         900

TGGCCCTGAT GAAGACCCCT GTCCTCTTTG ACGCTTATGA GATAAAGGAA         950

GCTATCAAGG GGGCGGGCAC TGATGAAGCC TGCCTGATCG AGATCCTGGC        1000

CTCCCGCAGC AACGAGCACA TCCGGGAGCT GAACAGAGTC TACAAGACAG        1050

AATTCAAAAA GACCCTGGAG GAGGCCATTC GGAGCGACAC TTCAGGGCAC        1100

TTCCAGCGGC TCCTCATCTC TCTCTCTCAG GGAAACCGGG ATGAAAGCAC        1150

AAACGTGGAC ATGACCCTTG TCCAGAGAGA TGTGCAGGAG CTCTATGCAG        1200

CTGGGGAGAA CCGCCTGGGA ACAGATGAGT CCAAGTTCAA TGCGATTCTG        1250

TGCTCCCGGA GCCGGGCCCA CCTGGTGGCA GTTTTTAACG AGTATCAGAG        1300

GATGACAGGA CGTGACATTG AGAAGAGCAT CTGCCGGGAG ATGTCCGGGG        1350

ACCTGGAGCA GGGCATGCTG GCTGTGGTGA AATGTCTTAA GAATACCCCA        1400

GCCTTCTTTG CTGAAAGGCT CAACAAGGCC ATGAGGGGAG CCGGAACCAA        1450

AGACCGGACC CTGATCCGCA TCATGGTGTC TCGCAGCGAG ATCGACCTCC        1500

TGGACATCAG AGCAGAGTAT AAGCGGCTGT ATGGCAAGTC GCTGTACCAC        1550

GACATCACGG GAGACACTTC AGGGGATTAC CGGAAGATTC TGCTGAAGAT        1600

CTGTGGTGGC AATGACTGAG CAGTGGCTGG TGGGTCACTT CTGTCCACCT        1650

GCTGGCAACA GCAATGCCAG GAAAAGGCCA AAAGAACGTT TGTCTGTTTC        1700

TAACAAATCT ACAAAGTAGC CCCCAGGTGT CACAGTTCAG ACCAACTGTA        1750

GAGCCTTGGC CCCATCTCCT CCCCCGCCCT CGATCCGTGC ATTGTGCTTG        1800

TGCCCGAGAA CCTAGTCAGT CTCGAACTCT CTCAGGACGC CTCCTCCCCA        1850
```

```
TCCCGACCCC TCACAGCCTC TTGCAGCTTA AAGTAGATGT TTTGTTCCTG        1900

AAAAATAAAC TCTGGCTTCC TCTAGTCATG TAGTTTTGTA TGTTTAGAGG        1950

TTTTTTTTTT TTTTTTAATA ATTAGTTGCA GACAGTTGCA TACACATCTT        2000

TGCTGCATAC AAAGTTTGGA TAAAAGAGGT GGGGGGTTGG AGTGCCATGT        2050

CTTCACTGAG GAGTAAAAGG AAAACTTTCA GGATAGACTC TGCATCTGGT        2100

GAAAATGTGT CATGAGCTTT GTTGTTGCCA AACTCACTCC TTTTTAGAAA        2150

AGAAAAGGCC AGAAAGTCAT CTGTTCTTTC TTCTACACAA ACCACAAGAA        2200

CAAAGCCAGC TCCCTGCCAG TGACAGGGCT TCTTGTAATT GAGAATGTGC        2250

CTTAACCTGA ATGTTGATGG CCAAATGCTG TTTCCAAATT AAAGTCTGCC        2300

AGCTCTGAAA A                                                  2311
```

(2) INFORMATION FOR SEQ ID NO: 4:

(i) SEQUENCE CHARACTERISTICS:
        (A) LENGTH: 505

(B) TYPE: amino acid
        (D) TOPOLOGY: Not Relevant (xi) SEQUENCE DESCRIPTION: SEQ ID NO: 4:

```
Met Ser Tyr Pro Gly Tyr Pro Pro Ala Gly Gly Tyr Pro Gly
              5                  10                  15

Ala Pro Gly Val Pro Glu Leu Glu Ser His Ala Gly Pro Gln Gly
            20                  25                  30

Leu Phe Ala Ala Met Asp Arg Ala Val Ser Asp Gly Pro Ala Met Met
        35                  40                  45

Leu Ala Ala Val Leu Leu Val Arg Ala Thr Ala Ala Asn Met Ser Gly
    50                  55                  60

Thr Phe Gly Gly Ala Asn Val Pro Asn Leu Tyr Pro Gly Ala Pro Gly
65                  70                  75                  80

Gly Gly Tyr Pro Pro Val Pro Pro Gly Gly Phe Gly Gln Pro Pro Pro
                85                  90                  95

Ala Gln Gln Pro Val Pro Ser Tyr Gly Met Tyr Pro Pro Gly Gly
            100                 105                 110

Asn Pro Thr Ser Gly Met Pro Ser Tyr Pro Pro Tyr Pro Gly Ala Pro
        115                 120                 125

Val Pro Gly Gln Pro Met Leu Pro Pro Gly Gln Gln Pro Pro Gly Val
    130                 135                 140

Tyr Pro Gly Gln Pro Pro Met Thr Tyr Pro Gly Gln Ser Pro Val Pro
145                 150                 155                 160

Pro Pro Gly Gln Gln Pro Val Pro Ser Tyr Pro Gly Tyr Ser Gly Ser
                165                 170                 175

Gly Thr Val Thr Pro Ala Val Ser Pro Ala Gln Phe Gly Asn Arg Gly
            180                 185                 190

Thr Ile Thr Asp Ala Ser Gly Phe Asp Pro Leu Arg Asp Ala Glu Val
        195                 200                 205

Leu Arg Lys Ala Met Lys Gly Phe Gly Thr Asp Glu Gln Ala Ile Ile
    210                 215                 220

Asp Cys Leu Gly Ser Arg Ser Asn Lys Gln Arg Gln Gln Ile Leu Leu
225                 230                 235                 240

Ser Phe Lys Thr Ala Tyr Gly Lys Asp Leu Ile Lys Asp Leu Lys Ser
                245                 250                 255
```

```
Glu Leu Ser Gly Asn Phe Glu Lys Thr Ile Leu Ala Leu Met Lys Thr
            260                 265                 270
Pro Val Leu Phe Asp Ala Tyr Glu Ile Lys Glu Ala Ile Lys Gly Ala
            275                 280                 285
Gly Thr Asp Glu Ala Cys Leu Ile Glu Ile Leu Ala Ser Arg Ser Asn
            290                 295                 300
Glu His Ile Arg Glu Leu Asn Arg Val Tyr Lys Thr Glu Phe Lys Lys
305                 310                 315                 320
Thr Leu Glu Glu Ala Ile Arg Ser Asp Thr Ser Gly His Phe Gln Arg
            325                 330                 335
Leu Leu Ile Ser Leu Ser Gln Gly Asn Arg Asp Glu Ser Thr Asn Val
            340                 345                 350
Asp Met Thr Leu Val Gln Arg Asp Val Gln Glu Leu Tyr Ala Ala Gly
            355                 360                 365
Glu Asn Arg Leu Gly Thr Asp Glu Ser Lys Phe Asn Ala Ile Leu Cys
            370                 375                 380
Ser Arg Ser Arg Ala His Leu Val Ala Val Phe Asn Glu Tyr Gln Arg
385                 390                 395                 400
Met Thr Gly Arg Asp Ile Glu Lys Ser Ile Cys Arg Glu Met Ser Gly
            405                 410                 415
Asp Leu Glu Gln Gly Met Leu Ala Val Val Lys Cys Leu Lys Asn Thr
            420                 425                 430
Pro Ala Phe Phe Ala Glu Arg Leu Asn Lys Ala Met Arg Gly Ala Gly
            435                 440                 445
Thr Lys Asp Arg Thr Leu Ile Arg Ile Met Val Ser Arg Ser Glu Ile
            450                 455                 460
Asp Leu Leu Asp Ile Arg Ala Glu Tyr Lys Arg Leu Tyr Gly Lys Ser
465                 470                 475                 480
Leu Tyr His Asp Ile Thr Gly Asp Thr Ser Gly Asp Tyr Arg Lys Ile
            485                 490                 495
Leu Leu Lys Ile Cys Gly Gly Asn Asp
            500                 505

(2) INFORMATION FOR SEQ ID NO:   5:

(i) SEQUENCE CHARACTERISTICS:
        (A) LENGTH:           29
        (B) TYPE:             nucleic acid
        (C) STRANDEDNESS:     single
        (D) TOPOLOGY:         linear (xi) SEQUENCE DESCRIPTION: SEQ ID NO: 5:

AGATCTAGCC ATGAGCTCCC CAGGCTACC                                    29

(2) INFORMATION FOR SEQ ID NO:   6:

(i) SEQUENCE CHARACTERISTICS:
        (A) LENGTH:           24
        (B) TYPE:             nucleic acid
        (C) STRANDEDNESS:     single
        (D) TOPOLOGY:         linear (xi) SEQUENCE DESCRIPTION: SEQ ID NO: 6:

CCCGCAGGTG GCTAGCCACC AGGT                                         24

(2) INFORMATION FOR SEQ ID NO:   7:

(i) SEQUENCE CHARACTERISTICS:
```

```
            (A) LENGTH:            25
            (B) TYPE:              nucleic acid
            (C) STRANDEDNESS:      single
            (D) TOPOLOGY:          linear (xi) SEQUENCE DESCRIPTION: SEQ ID NO: 7:

AGGTTTGGCA CGTTGGATCC TCCAA                                                  25

(2) INFORMATION FOR SEQ ID NO:     8:

(i) SEQUENCE CHARACTERISTICS:
            (A) LENGTH:            24
            (B) TYPE:              nucleic acid
            (C) STRANDEDNESS:      single
            (D) TOPOLOGY:          linear (xi) SEQUENCE DESCRIPTION: SEQ ID NO: 8:

CAACTATGCA GGGCAGTTCA ACCA                                                   24

(2) INFORMATION FOR SEQ ID NO:     9:

(i) SEQUENCE CHARACTERISTICS:
            (A) LENGTH:            27
            (B) TYPE:              nucleic acid
            (C) STRANDEDNESS:      single
            (D) TOPOLOGY:          linear (xi) SEQUENCE DESCRIPTION: SEQ ID NO: 9:

CCACATTATC CAGCCCAATG GGAGGCA                                                27

(2) INFORMATION FOR SEQ ID NO:     10:

(i) SEQUENCE CHARACTERISTICS:
            (A) LENGTH:            24
            (B) TYPE:              nucleic acid
            (C) STRANDEDNESS:      single
            (D) TOPOLOGY:          linear (xi) SEQUENCE DESCRIPTION: SEQ ID NO: 10:

AGCTGGAAAG CCACGCTGGA GGCC                                                   24

(2) INFORMATION FOR SEQ ID NO:     11:

(i) SEQUENCE CHARACTERISTICS:
            (A) LENGTH:            25
            (B) TYPE:              nucleic acid
            (C) STRANDEDNESS:      single
            (D) TOPOLOGY:          linear (xi) SEQUENCE DESCRIPTION: SEQ ID NO: 11:

TGGACAGGGC TGTTTCTGAC GGGCC                                                  25

(2) INFORMATION FOR SEQ ID NO:     12:

(i) SEQUENCE CHARACTERISTICS:
            (A) LENGTH:            28
            (B) TYPE:              nucleic acid
            (C) STRANDEDNESS:      single
            (D) TOPOLOGY:          linear (xi) SEQUENCE DESCRIPTION: SEQ ID NO: 12:

CAAGTAGCAC AGCAGCTAGC ATCATGGC                                               28

(2) INFORMATION FOR SEQ ID NO:     13:

(i) SEQUENCE CHARACTERISTICS:
            (A) LENGTH:            466
```

(B) TYPE: amino acid
(C) STRANDEDNESS: Not Relevant
(D) TOPOLOGY: Not Relevant (xi) SEQUENCE DESCRIPTION: SEQ ID NO: 13:

```
Met Ser Tyr Pro Gly Tyr Pro Thr Gly Tyr Pro Phe Pro Gly
            5                  10                 15

Tyr Pro Pro Ala Gly Gln Glu Ser Ser Phe Pro Ser Gly Gln Tyr
                20                  25              30

Pro Tyr Pro Ser Gly Phe Pro Pro Met Gly Gly Gly Ala Tyr Pro Gln
            35                  40                  45

Val Pro Ser Ser Gly Tyr Pro Gly Ala Gly Gly Tyr Pro Ala Pro Gly
 50                  55                  60

Gly Tyr Pro Ala Pro Gly Gly Tyr Pro Ala Pro Gln Pro Gly Gly
 65              70                  75                  80

Ala Pro Ser Tyr Pro Gly Val Pro Pro Gly Gln Gly Phe Gly Val Pro
                85                  90                  95

Pro Gly Gly Ala Gly Phe Ser Gly Tyr Pro Gln Pro Pro Ser Gln Ser
            100                 105                 110

Tyr Gly Gly Gly Pro Ala Gln Val Pro Leu Pro Gly Gly Phe Pro Gly
            115                 120                 125

Gly Gln Met Pro Ser Gln Tyr Pro Gly Gly Gln Pro Thr Tyr Pro Ser
130                 135                 140

Gln Pro Ala Thr Val Thr Gln Val Thr Gln Gly Thr Ile Arg Pro Ala
145                 150                 155                 160

Ala Asn Phe Asp Ala Ile Arg Asp Ala Glu Ile Leu Arg Lys Ala Met
                165                 170                 175

Lys Gly Phe Gly Thr Asp Glu Gln Ala Ile Val Asp Val Ala Asn
                180                 185                 190

Arg Ser Asn Asp Gln Arg Gln Lys Ile Lys Ala Ala Phe Lys Thr Ser
            195                 200                 205

Tyr Gly Lys Asp Leu Ile Lys Asp Leu Lys Ser Glu Leu Ser Gly Asn
    210                 215                 220

Met Glu Glu Leu Ile Leu Ala Leu Phe Met Pro Pro Thr Tyr Tyr Asp
225                 230                 235                 240

Ala Trp Ser Leu Arg Lys Ala Met Gln Gly Ala Gly Thr Gln Glu Arg
                245                 250                 255

Val Leu Ile Glu Ile Leu Cys Thr Arg Thr Asn Gln Glu Ile Arg Glu
            260                 265                 270

Ile Val Arg Cys Tyr Gln Ser Glu Phe Gly Arg Asp Leu Glu Lys Asp
            275                 280                 285

Ile Arg Ser Asp Thr Ser Gly His Phe Glu Arg Leu Leu Val Ser Met
    290                 295                 300

Cys Gln Gly Asn Arg Asp Glu Asn Gln Ser Ile Asn His Gln Met Ala
305                 310                 315                 320

Gln Glu Asp Ala Gln Arg Leu Tyr Gln Ala Gly Glu Gly Arg Leu Gly
                325                 330                 335

Thr Asp Glu Ser Cys Phe Asn Met Ile Leu Ala Thr Arg Ser Phe Pro
            340                 345                 350

Gln Leu Arg Ala Thr Met Glu Ala Tyr Ser Arg Met Ala Asn Arg Asp
            355                 360                 365

Leu Leu Ser Ser Val Ser Arg Glu Phe Ser Gly Tyr Val Glu Ser Gly
    370                 375                 380

Leu Lys Thr Ile Leu Gln Cys Ala Leu Asn Arg Pro Ala Phe Phe Ala
```

```
385                 390                 395                 400
Glu Arg Leu Tyr Tyr Ala Met Lys Gly Ala Gly Thr Asp Asp Ser Thr
                405                 410                 415

Leu Val Arg Ile Val Val Thr Arg Ser Glu Ile Asp Leu Val Gln Ile
            420                 425                 430

Lys Gln Met Phe Ala Gln Met Tyr Gln Lys Thr Leu Gly Thr Met Ile
            435                 440                 445

Ala Gly Asp Thr Ser Gly Asp Tyr Arg Arg Leu Leu Leu Ala Ile Val
        450                 455                 460

Gly Gln
465

(2) INFORMATION FOR SEQ ID NO:   14:

(i) SEQUENCE CHARACTERISTICS:
        (A) LENGTH:           319
        (B) TYPE:             amino acid
        (C) STRANDEDNESS: Not Relevant
        (D) TOPOLOGY: Not Relevant (xi) SEQUENCE DESCRIPTION: SEQ ID NO: 14:

Met Ala Ala Lys Gly Gly Thr Val Lys Ala Ala Ser Gly Phe Asn Ala
                5                   10                  15

Ala Glu Asp Ala Gln Thr Leu Arg Lys Ala Met Lys Gly Leu Gly Thr
            20                  25                  30

Asp Glu Asp Ala Ile Ile Asn Val Leu Ala Tyr Arg Ser Thr Ala Gln
        35                  40                  45

Arg Gln Glu Ile Arg Thr Ala Tyr Lys Thr Thr Ile Gly Arg Asp Leu
    50                  55                  60

Met Asp Asp Leu Lys Ser Glu Leu Ser Gly Asn Phe Glu Gln Val Ile
65                  70                  75                  80

Leu Gly Met Met Thr Pro Thr Val Leu Tyr Asp Val Gln Glu Leu Arg
                85                  90                  95

Lys Ala Met Lys Gly Ala Gly Thr Asp Glu Gly Cys Leu Ile Glu Ile
            100                 105                 110

Leu Ala Ser Arg Thr Pro Glu Glu Ile Arg Arg Ile Asn Gln Thr Tyr
        115                 120                 125

Gln Leu Gln Tyr Gly Arg Ser Leu Glu Asp Asp Ile Arg Ser Asp Thr
    130                 135                 140

Ser Phe Met Phe Gln Arg Val Leu Val Ser Leu Ser Ala Gly Gly Arg
145                 150                 155                 160

Asp Glu Ser Asn Tyr Leu Asp Asp Ala Leu Met Arg Gln Asp Ala Gln
                165                 170                 175

Asp Leu Tyr Glu Ala Gly Glu Lys Lys Trp Gly Thr Asp Glu Val Lys
            180                 185                 190

Phe Leu Thr Val Leu Cys Ser Arg Asn Arg Asn His Leu Leu His Val
        195                 200                 205

Phe Asp Glu Tyr Lys Arg Ile Ala Gln Lys Asp Ile Glu Gln Ser Ile
    210                 215                 220

Lys Ser Glu Thr Ser Gly Ser Phe Glu Asp Ala Leu Leu Ala Ile Val
225                 230                 235                 240

Lys Cys Met Arg Asn Lys Ser Ala Tyr Phe Ala Glu Arg Leu Tyr Lys
                245                 250                 255

Ser Met Lys Gly Leu Gly Thr Asp Asp Asp Thr Leu Ile Arg Val Met
            260                 265                 270
```

```
Val Ser Arg Ala Glu Ile Asp Met Leu Asp Ile Arg Ala Asn Phe Lys
        275                 280                 285

Arg Leu Tyr Gly Lys Ser Leu Tyr Ser Phe Ile Lys Gly Asp Thr Ser
        290                 295                 300

Gly Asp Tyr Arg Lys Val Leu Leu Ile Leu Cys Gly Gly Asp Asp
305                 310                 315
```

(2) INFORMATION FOR SEQ ID NO: 15:

(i) SEQUENCE CHARACTERISTICS:
        (A) LENGTH: 13
        (B) TYPE: amino acid
        (C) STRANDEDNESS: Not Relevant
        (D) TOPOLOGY: Not Relevant (xi) SEQUENCE DESCRIPTION: SEQ ID NO: 15:

```
Lys Ser Ser Lys Gly Gly Pro Gly Ser Ala Val Ser Pro
1               5                   10
```

(2) INFORMATION FOR SEQ ID NO: 16:

(i) SEQUENCE CHARACTERISTICS:
        (A) LENGTH: 13
        (B) TYPE: amino acid
        (C) STRANDEDNESS: Not Relevant
        (D) TOPOLOGY: Not Relevant (xi) SEQUENCE DESCRIPTION: SEQ ID NO: 16:

```
His Ser Thr Pro Pro Ser Ala Tyr Gly Ser Val Lys Ala
            5                   10
```

(2) INFORMATION FOR SEQ ID NO: 17:

(i) SEQUENCE CHARACTERISTICS:
        (A) LENGTH: 13
        (B) TYPE: amino acid
        (C) STRANDEDNESS: Not Relevant
        (D) TOPOLOGY: Not Relevant (xi) SEQUENCE DESCRIPTION: SEQ ID NO: 17:

```
Ala Ser Ile Trp Val Gly His Arg Gly Thr Val Arg Asp
            5                   10
```

(2) INFORMATION FOR SEQ ID NO: 18:

(i) SEQUENCE CHARACTERISTICS:
        (A) LENGTH: 10
        (B) TYPE: amino acid
        (C) STRANDEDNESS: Not Relevant
        (D) TOPOLOGY: Not Relevant (xi) SEQUENCE DESCRIPTION: SEQ ID NO: 18:

```
Met Ala Ala Lys Gly Gly Thr Val Lys Ala
            5                   10
```

(2) INFORMATION FOR SEQ ID NO: 19:

(i) SEQUENCE CHARACTERISTICS:
        (A) LENGTH: 11
        (B) TYPE: amino acid
        (C) STRANDEDNESS: Not Relevant
        (D) TOPOLOGY: Not Relevant (xi) SEQUENCE DESCRIPTION: SEQ ID NO: 19:

```
Met Ala Gln Val Leu Arg Gly Thr Val Thr Asp
            5                   10
```

(2) INFORMATION FOR SEQ ID NO: 20:

(i) SEQUENCE CHARACTERISTICS:
        (A) LENGTH:         13
        (B) TYPE:           amino acid
        (C) STRANDEDNESS: Not Relevant
        (D) TOPOLOGY: Not Relevant (xi) SEQUENCE DESCRIPTION: SEQ ID NO: 20:

Pro Ala Gln Gly Ala Lys Tyr Arg Gly Ser Ile His Asp
                 5                  10

(2) INFORMATION FOR SEQ ID NO: 21:

(i) SEQUENCE CHARACTERISTICS:
        (A) LENGTH:         13
        (B) TYPE:           amino acid
        (C) STRANDEDNESS: Not Relevant
        (D) TOPOLOGY: Not Relevant (xi) SEQUENCE DESCRIPTION: SEQ ID NO: 21:

Ala Val Ala Arg Val Glu Leu Lys Gly Thr Val Arg Pro
                 5                  10

(2) INFORMATION FOR SEQ ID NO: 22:

(i) SEQUENCE CHARACTERISTICS:
        (A) LENGTH:         13
        (B) TYPE:           amino acid
        (C) STRANDEDNESS: Not Relevant
        (D) TOPOLOGY: Not Relevant (xi) SEQUENCE DESCRIPTION: SEQ ID NO: 22:

Ala Thr Val Thr Gln Val Thr Gln Gly Thr Ile Arg Pro
                 5                  10

(2) INFORMATION FOR SEQ ID NO: 23:

(i) SEQUENCE CHARACTERISTICS:
        (A) LENGTH:         13
        (B) TYPE:           amino acid
        (C) STRANDEDNESS: Not Relevant
        (D) TOPOLOGY: Not Relevant (xi) SEQUENCE DESCRIPTION: SEQ ID NO: 23:

Lys Ser Trp Ile Glu Gln Glu Gly Val Thr Val Lys Ser
                 5                  10

(2) INFORMATION FOR SEQ ID NO: 24:

(i) SEQUENCE CHARACTERISTICS:
        (A) LENGTH:         13
        (B) TYPE:           amino acid
        (C) STRANDEDNESS: Not Relevant
        (D) TOPOLOGY: Not Relevant (xi) SEQUENCE DESCRIPTION: SEQ ID NO: 24:

Glu Asp Phe Gly Val Asn Glu Asp Leu Ala Asp Ser Asp
                 5                  10

(2) INFORMATION FOR SEQ ID NO: 25:

(i) SEQUENCE CHARACTERISTICS:
        (A) LENGTH:         14
        (B) TYPE:           amino acid
        (C) STRANDEDNESS: Not Relevant
        (D) TOPOLOGY: Not Relevant (xi) SEQUENCE DESCRIPTION: SEQ ID NO: 25:

Glu Asp Gly Ser Val Ile Asp Tyr Glu Leu Ile Asp Gln Asp
              5                   10

(2) INFORMATION FOR SEQ ID NO:   26:

(i) SEQUENCE CHARACTERISTICS:
        (A) LENGTH:           13
        (B) TYPE:             amino acid
        (C) STRANDEDNESS: Not Relevant
        (D) TOPOLOGY: Not Relevant (xi) SEQUENCE DESCRIPTION: SEQ ID NO: 26:

Glu Ser Leu Lys Val Asp Glu His Leu Ala Lys Gln Asp
              5                   10

(2) INFORMATION FOR SEQ ID NO:   27:

(i) SEQUENCE CHARACTERISTICS:
        (A) LENGTH:           13
        (B) TYPE:             amino acid
        (C) STRANDEDNESS: Not Relevant
        (D) TOPOLOGY: Not Relevant (xi) SEQUENCE DESCRIPTION: SEQ ID NO: 27:

Glu Ser Asn Tyr Leu Asp Asp Ala Leu Met Arg Gln Asp
              5                   10

(2) INFORMATION FOR SEQ ID NO:   28:

(i) SEQUENCE CHARACTERISTICS:
        (A) LENGTH:           13
        (B) TYPE:             amino acid
        (C) STRANDEDNESS: Not Relevant
        (D) TOPOLOGY: Not Relevant (xi) SEQUENCE DESCRIPTION: SEQ ID NO: 28:

Pro Asp Ala Gly Ile Asp Glu Ala Gln Val Glu Gln Asp
              5                   10

(2) INFORMATION FOR SEQ ID NO:   29:

(i) SEQUENCE CHARACTERISTICS:
        (A) LENGTH:           13
        (B) TYPE:             amino acid
        (C) STRANDEDNESS: Not Relevant
        (D) TOPOLOGY: Not Relevant (xi) SEQUENCE DESCRIPTION: SEQ ID NO: 29:

Glu Asp Asp Val Val Ser Glu Asp Leu Val Gln Gln Asp
              5                   10

(2) INFORMATION FOR SEQ ID NO:   30:

(i) SEQUENCE CHARACTERISTICS:
        (A) LENGTH:           13
        (B) TYPE:             amino acid
        (C) STRANDEDNESS: Not Relevant
        (D) TOPOLOGY: Not Relevant (xi) SEQUENCE DESCRIPTION: SEQ ID NO: 30:

Leu Asp Gln Ala Arg Glu Asp Ala Gln Val Ala Ala Glu
              5                   10

(2) INFORMATION FOR SEQ ID NO:   31:

(i) SEQUENCE CHARACTERISTICS:

```
          (A) LENGTH:         13
          (B) TYPE:           amino acid
          (C) STRANDEDNESS: Not Relevant
          (D) TOPOLOGY: Not Relevant (xi) SEQUENCE DESCRIPTION: SEQ ID NO: 31:

Glu Asn Gln Ser Ile Asn His Gln Met Ala Gln Glu Asp
              5                   10

(2) INFORMATION FOR SEQ ID NO:   32:

(i) SEQUENCE CHARACTERISTICS:
          (A) LENGTH:         14
          (B) TYPE:           amino acid
          (C) STRANDEDNESS: Not Relevant
          (D) TOPOLOGY: Not Relevant (xi) SEQUENCE DESCRIPTION: SEQ ID NO: 32:

Asp Val Ser Ser Phe Val Asp Pro Ala Leu Ala Leu Gln Asp
              5                   10

(2) INFORMATION FOR SEQ ID NO:   33:

(i) SEQUENCE CHARACTERISTICS:
          (A) LENGTH:         22
          (B) TYPE:           nucleic acid
          (C) STRANDEDNESS:   single
          (D) TOPOLOGY:       linear (xi) SEQUENCE DESCRIPTION: SEQ ID NO: 33:

CCAGGTGCAC CAGGTAAGAA GG                                                      22

(2) INFORMATION FOR SEQ ID NO:   34:

(i) SEQUENCE CHARACTERISTICS:
          (A) LENGTH:         51
          (B) TYPE:           nucleic acid
          (C) STRANDEDNESS:   single
          (D) TOPOLOGY:       linear (xi) SEQUENCE DESCRIPTION: SEQ ID NO: 34:

CTGGGGAGCT CTGTCCTAGG TGTCCCGGAG GTGAGGGCTA CGGTGAGGGC T                       51

(2) INFORMATION FOR SEQ ID NO:   35:

(i) SEQUENCE CHARACTERISTICS:
          (A) LENGTH:         51
          (B) TYPE:           nucleic acid
          (C) STRANDEDNESS:   single
          (D) TOPOLOGY:       linear (xi) SEQUENCE DESCRIPTION: SEQ ID NO: 35:

GACTGGGTGT TGCTTTCAGG TGGCGGTGCC CTCTCAGGAG TGGTGAGTCC A                       51

(2) INFORMATION FOR SEQ ID NO:   36:

(i) SEQUENCE CHARACTERISTICS:
          (A) LENGTH:         31
          (B) TYPE:           nucleic acid
          (C) STRANDEDNESS:   single
          (D) TOPOLOGY:       linear (xi) SEQUENCE DESCRIPTION: SEQ ID NO: 36:

CTGCTTTGTG GACTTTCAGG CGGCCAACAT G                                             31
```

We claim:

1. An isolated nucleic acid encoding a polypeptide having at least 90% identity to the amino acid sequence of bovine annexin type I (SEQ ID NO:2) or bovine annexin XI type II (SEQ ID NO:4), said polypeptide being capable of binding phospholipid and $Ca^{2+}$, said polypeptide further being capable of inhibiting phospholiphase $A_2$.

2. The nucleic acid of claim 1, said nucleic acid encoding human annexin XI.

3. A plasmid comprising the nucleic acid of claim 1.

4. The plasmid of claim 3, said plasmid further comprising an expression control sequence capable of directing expression of said annexin XI.

5. A cell comprising the plasmid of claim 4.

6. The cell of claim 5 wherein said cell is a prokaryotic cell.

7. The cell of claim 5 wherein said cell is a eukaryotic cell.

8. The cell of claim 7 wherein said cell is mammalian cell.

9. An isolated nucleic acid encoding a polypeptide having the amino acid sequence of bovine annexin XI type I (SEQ ID NO:2) or bovine annexin XI type II (SEQ ID NO:4).

* * * * *

UNITED STATES PATENT AND TRADEMARK OFFICE
CERTIFICATE OF CORRECTION

PATENT NO. : 6,107,089
DATED : AUGUST 22, 2000
INVENTOR(S) : CHRISTINE A TOWLE; BENJAMIN V. TREADWELL

It is certified that error appears in the above-identified patent and that said Letters Patent is hereby corrected as shown below:

Column 2, Line 9, Delete "CDNA" and insert - - c DNA- -

Column 5, Line 21, Delete "FIG.1 panel A" and insert - - FIGS 1A and 1 B- -

Column 5, Line 22, Delete " [and] of clone pCT101. Fig. 1. panel B depicts the" and insert - - and- -

Column 7, Line 16, Delete "[in conjunction with]" and "[was used]"

Signed and Sealed this

First Day of May, 2001

NICHOLAS P. GODICI

*Attest:*

*Attesting Officer*   Acting Director of the United States Patent and Trademark Office